(12) United States Patent
Siffert

(10) Patent No.: US 6,924,100 B2
(45) Date of Patent: Aug. 2, 2005

(54) GENE ALTERATION IN THE GENE FOR THE Gβ3-SUBUNIT OF THE HUMAN G PROTEIN

(76) Inventor: Winfried Siffert, Schönleinstrasse 49, Essen (DE), D-45147

( * ) Notice: Subject to any disclaimer, the term of this patent is extended or adjusted under 35 U.S.C. 154(b) by 87 days.

(21) Appl. No.: 09/803,653

(22) Filed: Mar. 12, 2001

(65) Prior Publication Data

US 2002/0086297 A1 Jul. 4, 2002

Related U.S. Application Data

(63) Continuation-in-part of application No. PCT/EP99/06534, filed on Sep. 6, 1999.

(30) Foreign Application Priority Data

| | | |
|---|---|---|
| Sep. 10, 1998 | (DE) | 198 41 299 |
| Feb. 5, 1999 | (DE) | 199 04 825 |
| Mar. 18, 1999 | (DE) | 199 12 049 |
| Mar. 29, 1999 | (DE) | 199 14 229 |
| Apr. 30, 1999 | (DE) | 199 19 989 |
| May 21, 1999 | (DE) | 199 23 539 |

(51) Int. Cl.$^7$ ................................................ C12Q 1/68
(52) U.S. Cl. ............................. 435/6; 435/4; 536/23.5; 536/24.31; 536/24.33
(58) Field of Search ............................. 435/6, 7, 91.2; 536/24.31, 23.1, 23.5

(56) References Cited

PUBLICATIONS

Serretti et al. American Journal of Medical Genetics. 2002. 114: 370–379.*
Naber et al. FEBS Letters. (200) 484: 199–201.*
Zill et al. NeuroReport. Jun. 2000. 11: 1893–1897.*
Grossman et al. Pharcogenetics. Jun. 2001, 11: 307–316.*

* cited by examiner

Primary Examiner—Carla J. Myers
(74) Attorney, Agent, or Firm—Nixon Peabody LLP

(57) ABSTRACT

Use of a gene change in the gene for the Gβ3 subunit of the human G protein, at position 825 in SEQ ID No. 2 with a substitution of cytosine by thymine and/or at position 1429 in SEQ ID No. 2 there being substitution of cytosine by thymine, for determination of the risk of contracting a disease which is associated with G protein dysregulation.

11 Claims, 23 Drawing Sheets

Enhanced Chemotaxis of T-Lymphocytes from 825T Allele Carriers

Event: CD4 Cell Count Below 200 per µl

Event: Lowest CD4 Cell Count

Event: Time to maximum HIV Virus Load

Virus Copy Number determined by Quantitative PCR

Potential Structures of Gβ3 and Gβ3s / Gβ3s-2

FIG. 17

ß3-original sequence of Levine. The exons are underlined alternately. The area which is omitted by cryptic splice as bold-faced.

```
1    gggtcgATGG GGGAGATGGA GCAACTGCGT CAGGAAGCGG AGCAGCTCAA GAAGCAGATT
     Start-ATG   EXON 3 after Ansari-Lari
     Nucleotide 1-6 seem not to be affected 61   GCAGATGCCA GGAAAGCCTG TGCTGACGTT ACTCTGGCAG AGCTGGTGTC TGGCCTAGAG
        /Beginning EXON 4                         /EXON 5 Beginning
                                                  ==> ENDE 1 KLON ANSARI 121  GTGGTGGGAC GAGTCCAGAT GCGGACGCGG CGGACGTTAA GGGGACACCT GGCCAAGATT
     EXON 5

181  TACGCCATGC ACTGGGCCAC TGATTCTAAG CTGCTGGTAA GTGCCTCGCA AGATGGGAAG
     EXON 5                                       / Beginning EXON 6

241  CTGATCGTGT GGGACAGCTA CACCACCAAC AAGGTGCACG CCATCCCACT GCGCTCCTCC
     EXON 6                                       / EXON 7

301  TGGGTCATGA CCTGTGCCTA TGCCCCATCA GGGAACTTTG TGGCATGTGG GGGGCTGGAC
     EXON 7

361  AACATGTGTT CCATCTACAA CCTCAAATCC CGTGAGGGCA ATGTCAAGGT CAGCCGGGAG
     EXON 7

421  CTTTCTGCTC ACACAGGTTA TCTCTCCTGC TGCCGCTTCC TGGATGACAA CAATATTGTG
     EXON 7      /EXON 8

481  ACCAGCTCGG GGACACCAC GTGTGCCTTG TGGGACATTG AGACTGGGCA GCAGAAGACT
     EXON 8                /EXON 9
                           cryptic SPLICING
541  GTATTTGTGG GACACACGGG TGACTGCATG AGCCTGGCTG TGTCTCCTGA CTTCAATCTC
     EXON 9
     cryptic SPLICING 601  TTCATTTCGG GGGCCTGTGA TGCCAGTGCC AAGCTCTGGG ATGTGCGAGA GGGGACCTGC
     EXON 9
        cryptic SPLICING   /

661  CGTCAGACTT TCACTGGCCA CGAGTCGGAC ATCAACGCCA TCTGTTTCTT CCCCAATGGA
     EXON 9                                       / Beginning EXON 10

721  GAGGCCATCT GCACGGGCTC GGATGACGCT TCCTGCCGCT TGTTTGACCT GCGGGCAGAC
     EXON 10
```

FIG. 17(cont.)

```
 781 CAGGAGCTGA TCTGCTTCTC CCACGAGAGC ATCATCTGCG GCATCACGTC CGTGGCCTTC
     EXON 10           Polymorphism site                    acgtc tgt 841 TCCCTCAGTG GCCGCCTACT ATTCGCTGGC TACGACGACT TCAACTGCAA TGTCTGGGAC
     EXON 10

901 TCCATGAAGT CTGAGCGTGT GGGCATCCTC TCTGGCCACG ATAACAGGGT GAGCTGCCTG
     EXON 10           /Beginning EXON 11

961 GGAGTCACAG CTGACGGGAT GGCTGTGGCC ACAGGTTCCT GGGACAGCTT CCTCAAAATC
     EXON 11

1021 TGGAACTGAg gaggctggag aaagggaagt ggaaggcagt gaacacactc agcagccccc
     EXON 11
             End of Open Reading Frame 1081 tgcccgaccc catctcattc aggtgttctc ttctatattc cgggtgccat tcccactaag
     EXON 11

1141 ctttctcctt tgagggcagt ggggagcatg ggactgtgcc tttgggaggc agcatcaggg
     EXON 11

1201 acacaggggc aaagaactgc cccatctcct cccatggcct tccctcccca cagtcctcac
     EXON 11

1261 agcctctccc ttaatgagca aggacaacct gcccctcccc agccctttgc aggcccagca
     EXON 11

1321 gacttgagtc tgaggcccca ggccctagga ttcctccccc agagccacta cctttgtcca
     EXON 11
                                                    "Ban Polymorphismus"
                                                    tctggcactja cta
1381 ggcctgggtg gtatagggcg tttggccctg tgactatggc tctggcacca ctagggtcct
     EXON 11

1441 ggccctcttc ttattcatgc tttctccttt ttctaccttt ttttctctcc taagacacct
     EXON 11

1501 gcaataaagt gtagcaccct ggt
     EXON 11      POLY A SITE
```

FIG. 18

Sequence with two polymorphisms (Numbering after the Levine sequence)

| | | | | | | |
|---|---|---|---|---|---|---|
| gggtcgatgg | gggagatgga | gcaactgcgt | caggaagcgg | agcagctcaa | gaagcagatt | 60 |
| gcagatgcca | ggaaagcctg | tgctgacgtt | actctggcag | agctggtgtc | tggcctagag | 120 |
| gtggtgggac | gagtccagat | cggacgcgg | cggacgttaa | ggggacacct | ggccaagatt | 180 |
| tacgccatgc | actgggccac | tgattctaag | ctgctggtaa | gtgcctcgca | agatgggaag | 240 |
| ctgatcgtgt | gggacagcta | caccaccaac | aaggtgcacg | ccatcccact | gcgctcctcc | 300 |
| tgggtcatga | cctgtgccta | tgcccatca | gggaactttg | tggcatgtgg | ggggctggac | 360 |
| aacatgtgtt | ccatctacaa | cctcaaatcc | cgtgagggca | atgtcaaggt | cagccgggag | 420 |
| ctttctgctc | acacaggtta | tctctcctgc | tgccgcttcc | tggatgacaa | caatattgtg | 480 |
| accagctgg | gggacaccac | gtgtgccttg | tgggacattg | agactgggca | gcagaagact | 540 |
| gtatttgtgg | gacacacggg | tgactgcatg | agcctggctg | tgtctcctga | cttcaatctc | 600 |
| ttcatttcgg | gggctgtga | tgccagtgcc | aagctctggg | atgtgcgaga | ggggacctgc | 660 |
| cgtcagactt | tcactggcca | cgagtcggac | atcaacgcca | tctgtttctt | ccccaatgga | 720 |
| gaggccatct | gcacgggctc | ggatgacgct | tcctgccgct | tgtttgacct | gggggcagac | 780 |
| caggagctga | tctgcttctc | ccacgagagc | atcatctgcg | gcatcacgtc | tgtggccttc | 840 |
| tccctcagtg | gccgcctact | attcgctggc | tacgacgact | tcaactgcaa | tgtctgggac | 900 |
| tccatgaagt | ctgagcgtgt | gggcatcctc | tctggccacg | ataacagggt | gagctgcctg | 960 |
| ggagtcacag | ctgacgggat | ggctgtggcc | acaggttcct | gggacagctt | cctcaaaatc | 1020 |
| tggaactgag | gaggctggag | aaagggaagt | ggaaggcagt | gaacacactc | agcagccccc | 1080 |
| tgcccgaccc | catctcattc | aggtgttctc | ttctatattc | cgggtgccat | tccactaag | 1140 |
| ctttctcctt | tgagggcagt | ggggagcatg | ggactgtgcc | tttgggaggc | agcatcaggg | 1200 |
| acacaggggc | aaagaactgc | cccatctcct | cccatggcct | tccctcccca | cagtcctcac | 1260 |
| agcctctccc | ttaatgagca | aggacaacct | gccccctcccc | agcctttgc | aggcccagca | 1320 |
| gacttgagtc | tgaggcccca | ggccctagga | ttcctccccc | agagccacta | cctttgtcca | 1380 |
| tctggcacta | ctaggcctgg | gtggtatagg | gcgtttggcc | ctgtgactat | ggctctggca | 1440 |
| ccactagggt | cctggccctc | ttcttattca | tgctttctcc | ttttctacc | tttttctc | 1500 |
| toctaagaca | cctgcaataa | agtgtagcac | cctggt | | | 1536 |

FIG. 19

Nucleic acid sequence of cDNA of Gß3 and description of the deletion in Gß3 and Gß3s-2. Numbering referenced to the cDNA of Levine et al.(Levine, M.A., Smallwood, P.M., Moen, P.T.Jr., Helman, L.J., and Ahn, T.G. Molecular cloning of ß3 subunit, a third form of the G protein beta-subunit polypeptide. *Proc.Natl.Acad.Sci.USA* 87(6):2329-2333, 1990) Here numbering does not begin with start codon ATG, but 6 nucleotides earlier in the 5' area.

```
1    gggtcgATGG GGGAGATGGA GCAACTGCGT CAGGAAGCGG AGCAGCTCAA GAAGCAGATT
     Start-ATG   EXON 3
     Nucleotide 1-6 seem not to be affected 61   GCAGATGCCA GGAAAGCCTG TGCTGACGTT ACTCTGGCAG AGCTGGTGTC TGGCCTAGAG
     /Beginn EXON 4                                         /EXON 5 Beginning 121  GTGGTGGGAC GAGTCCAGAT GCGGACGCGG CGGACGTTAA GGGGACACCT GGCCAAGATT
     EXON 5

181  TACGCCATGC ACTGGGCCAC TGATTCTAAG CTGCTGGTAA GTGCCTCGCA AGATGGGAAG
     EXON 5                                   / Beginning EXON 6

241  CTGATCGTGT GGGACAGCTA CACCACCAAC AAGGTGCACG CCATCCCACT GCGCTCCTCC
     EXON 6                                    / EXON 7

301  TGGGTCATGA CCTGTGCCTA TGCCCCATCA GGGAACTTTG TGGCATGTGG GGGGCTGGAC
     EXON 7

361  AACATGTGTT CCATCTACAA CCTCAAATCC CGTGAGGGCA ATGTCAAGGT CAGCCGGGAG
     EXON 7

421  CTTTCTGCTC ACACAGGTTA TCTCTCCTGC TGCCGCTTCC TGGATGACAA CAATATTGTG
     EXON 7      /EXON 8
                                     Deletion bei Gß3s
481  ACCAGCTCGG GGACACCAC GTGTGCCTTG TGGGACATTG AGACTGGGCA GCAGAAGACT
     EXON 8                    /EXON 9

541  GTATTTGTGG GACACACGGG TGACTGCATG AGCCTGGCTG TGTCTCCTGA CTTCAATCTC
     EXON 9

601  TTCATTTCGG GGGCCTGTGA TGCCAGTGCC AAGCTCTGGG ATGTGCGAGA GGGGACCTGC
     EXON 9
                                                 Deletion in Gß3s2
661  CGTCAGACTT TCACTGGCCA CGAGTCGGAC ATCAACGCCA TCTGTTTCTT CCCCAATGGA
     EXON 9                                            / Beginn EXON 10
                                                 Intron dazwischen 1607 bp
```

FIG. 19(cont.)

```
     ┌Deletion in Gβ3s2─────────────────────────────────────────────┐
721  │GAGGCCATCT GCACGGGCTC GGATGACGCT TCCTGCCGCT TGTTTGACCT GCGGGCAGAC│
     EXON 10

┌─────────────────────────────────────────────────────────────┐
781  │CAGGAGCTGA TCTGCTTCTC CCACGAGAGC ATCATCTGCG GCATCACGTC CGTGGCCTTC│
     EXON 10                      · polymorphism site      agtc tgt 841  TCCCTCAGTG GCCGCCTACT ATTCGCTGGC TACGACGACT TCAACTGCAA TGTCTGGGAC
     EXON 10

901  TCCATGAAGT CTGAGCGTGT GGGCATCCTC TCTGGCCACG ATAACAGGGT GAGCTGCCTG
     EXON 10            /Beginning EXON 11 (Intron dazw. 989 bp)

961  GGAGTCACAG CTGACGGGAT GGCTGTGGCC ACAGGTTCCT GGGACAGCTT CCTCAAAATC
     EXON 11

1021 TGGAACTGAg gaggctggag aaagggaagt ggaaggcagt gaacacactc agcagcccc
     EXON 11
             End of Open Reading Frame B3-3

1081 tgcccgaccc catctcattc aggtgttctc ttctatattc cgggtgccat tcccactaag
     EXON 11

1141 ctttctcctt tgagggcagt ggggagcatg ggactgtgcc tttgggaggc agcatcaggg
     EXON 11

1201 acacagggc aaagaactgc cccatctcct cccatggcct tccctcccca cagtcctcac
     EXON 11

1261 agcctctccc ttaatgagca aggacaacct gcccctcccc agccctttgc aggcccagca
     EXON 11

1321 gacttgagtc tgaggcccca ggccctagga ttcctccccc agagccacta cctttgtcca
     EXON 11
                                                       ┌C1423T┐
                                               tctggcad│t│a cta
1381 ggcctggggtg gtatagggcg tttggccctg tgactatggc tctggcad│c│a ctagggtcct
     EXON 11

1441 ggccctcttc ttattcatgc tttctccttt ttctaccttt ttttctctcc taagacacct
     EXON 11

1501 gcaataaagt gtagcaccct ggt
     EXON 11     POLY A SITE
```

FIG. 20

Amino acid sequence of Gβ3s-2 (Combined production)

```
atg ggg gag atg gag caa ctg cgt cag gaa gcg gag cag ctc aag aag    48
Met Gly Glu Met Glu Gln Leu Arg Gln Glu Ala Glu Gln Leu Lys Lys
              5                   10              15 cag att gca gat gcc agg aaa gcc tgt gct gac gtt act ctg gca gag    96
Gln Ile Ala Asp Ala Arg Lys Ala Cys Ala Asp Val Thr Leu Ala Glu
             20              25              30 ctg gtg tct ggc cta gag gtg gtg gga cga gtc cag atg cgg acg cgg   144
Leu Val Ser Gly Leu Glu Val Val Gly Arg Val Gln Met Arg Thr Arg
             35              40              45 cgg acg tta agg gga cac ctg gcc aag att tac gcc atg cac tgg gcc   192
Arg Thr Leu Arg Gly His Leu Ala Lys Ile Tyr Ala Met His Trp Ala
             50              55              60 act gat tct aag ctg ctg gta agt gcc tcg caa gat ggg aag ctg atc   240
Thr Asp Ser Lys Leu Leu Val Ser Ala Ser Gln Asp Gly Lys Leu Ile
65              70              75              75 gtg tgg gac agc tac acc acc aac aag gtg cac gcc atc cca ctg cgc   288
Val Trp Asp Ser Tyr Thr Thr Asn Lys Val His Ala Ile Pro Leu Arg
             80              85              90 tcc tcc tgg gtc atg acc tgt gcc tat gcc cca tca ggg aac ttt gtg   336
Ser Ser Trp Val Met Thr Cys Ala Tyr Ala Pro Ser Gly Asn Phe Val
             95             100             105 gca tgt ggg ggg ctg gac aac atg tgt tcc atc tac aac ctc aaa tcc   384
Ala Cys Gly Gly Leu Asp Asn Met Cys Ser Ile Tyr Asn Leu Lys Ser
            110             115             120 cgt gag ggc aat gtc aag gtc agc cgg gag ctt tct gct cac aca ggt   432
Arg Glu Gly Asn Val Lys Val Ser Arg Glu Leu Ser Ala His Thr Gly
            125             130             135 tat ctc tcc tgc tgc cgc ttc ctg gat gac aac aat att gtg acc agc   480
Tyr Leu Ser Cys Cys Arg Phe Leu Asp Asp Asn Asn Ile Val Thr Ser
140             145             150             155
```

FIG. 20(cont.)

```
tcg ggg gac acc acg tgt gcc ttg tgg gac att gag act ggg cag cag    528
Ser Gly Asp Thr Thr Cys Ala Leu Trp Asp Ile Glu Thr Gly Gln Gln
160             165             170             175 aag act gta ttt gtg gga cac acg ggt gac tgc atg agc ctg gct gtg    576
Lys Thr Val Phe Val Gly His Thr Gly Asp Cys Met Ser Leu Ala Val
                180             185             190 tct cct gac ttc aat ctc ttc att tcg ggg gcc tgt gat gcc agt gcc    624
ser Pro Asp Phe Asn Leu Phe Ile Ser Gly Ala Cys Asp Ala Ser Ala
            195             200             205 aag ctc tgg gat gtg cga gag ggg acc tgc cgt cag act ttc act ggc    672
Lys Leu Trp Asp Val Arg Glu Gly Thr Cys Arg Gln Thr Phe Thr Gly
        210             215             220 cag gag tcg gac atc aac gcc atc tgt ttc ttc tcc ctc agt ggc cgc    720
His Glu Ser Asp Ile Asn Ala Ile Cys Phe Phe Ser Leu Ser Gly Arg
225             230             235 cta cta ttc gct ggc tac gac gac ttc aac tgc aat gtc tgg gac tcc    768
Leu Leu Phe Ala Gly Tyr Asp Asp Phe Asn Cys Asn Val Trp Asp Ser
240             245             250             255 atg aag tct gag cgt gtg ggc atc ctc tct ggc cac gat aac agg gtg    816
Met Lys Ser Glu Arg Val Gly Ile Leu Ser Gly His Asp Asn Arg Val
            260             265             270 agc tgc ctg gga gtc aca gct gac ggg atg gct gtg gcc aca ggt tcc    864
Ser Cys Leu Gly Val Thr Ala Asp Gly Met Ala Val Ala Thr Gly Ser
        275             280             285 tgg gac agc ttc ctc aaa atc tgg aac tga                            894
Trp Asp Ser Phe Leu Lys Ile Trp Asn ***
290             295
```

GENE ALTERATION IN THE GENE FOR THE Gβ3-SUBUNIT OF THE HUMAN G PROTEIN

CROSS-REFERENCES TO RELATED APPLICATIONS

This is a continuation-in-part of international patent application PCT/EP/99/06534, filed Sep. 6, 1999, designating the United States.

BACKGROUND OF THE INVENTION

1. Field of the Invention

This invention relates to a novel nucleic acid sequence coding for the Gβ3-subunit of the human G protein and the use of the Gβ3 subunits of the G proteins for determining the risk of contracting a disease which is associated with a G protein dysregulation.

2. Description of Related Art

Heterotrimeric guanine nucleotide-binding proteins (G proteins) are of outstanding importance in intracellular signal transduction. They mediate the relay of extracellular signals after stimulation of hormone receptors and other receptors which undergo a conformation change after receptor activation. This leads to activation of G proteins which subsequently can activate or inhibit intracellular effectors (for example, ion channels, enzymes). G proteins control intracellular signal processing after hormone stimulation of heptahelical receptors in the cell membrane, but also after stimulation of receptors with intrinsic tyrosine kinase activity. Regulated cell functions include among others cell division and cell growth, contraction, release of cell contents, and much more.

Heterotrimeric G proteins are composed of three subunits, the alpha, beta and gamma subunits. To date several different alpha subunits, 5 beta subunits and roughly 12 gamma subunits have been detected using biochemical and molecular biological methods (Bimbaumer, L. and Bimbaumer, M., Signal transduction by G proteins: 1994 edition. J. Recept. Res. 15: 213–252, 1995; Offermans, S. and Schultz, G. Complex information processing by the transmembrane signalling system involving G proteins. Naunym Schmiedebergs Arch. Pharmacol. 350: 329–338, 1994; Nuernberg, B., Gudermann, T. and Schultz, G. Receptors and G proteins as primary components of transmembrane signal transduction. Part 2, G proteins: structure and function. J. Mol. Med. 73:123–132, 1995; Neer, E. J. Heterotrimeric G protein: Organizers of Transmembrane Signals. Cell 80: 249–257, 1995; Rens-Domiano, S. and Hamm, H. E. Structural and functional relationships of heterotrimeric G proteins. FASEB J. 9: 1059–1066, 1995).

The receptor-mediated activation of certain alpha subunits can be inhibited by pretreatment with pertussis toxin (PTX). They include especially the alpha isoforms alpha-11, alpha-12 and alpha-13 and different alphao-subunits. These G proteins are also called "PTX-sensitive G proteins".

Betagamma subunits perform important functions in G protein activation and in the modulation of intracellular reactions. All previously known G protein beta subunits on the level of the nucleotide sequence and on the level of the amino acid sequence have high homologies. In this respect these similarities are found not only within the human beta subunits (Gβ1, Gβ2, Gβ3), but also in comparison with beta subunits of other species, for example fruit flies or yeasts.

Recently a base change in exon 10 (C825T) which leads to alternative splicing of exon 9 was described in the human GNB3 gene which codes for the Gβ3 subunit. Alternative splicing is promoted by a cryptic splice site in exon 9, the base exchange C825T which is located farther away intensifying the splicing. The alternative splice product (Gβ3s) has a loss of 123 bp (=41 amino acids). The GNB3-825T allele is associated with increased activation capacity of G proteins and essential hypertension (Siffert, W., Rosskopf, D., Siffert, G., Busch, S., Moritz, A., Erbel, R., Sharma, A. M., Ritz, E.; Wichmann, H. E., Jakobs, K. H., and Horsthemke, B. Association of a human G protein β3 subunit variant with hypertension. Nat. Genet. 18(1): 45–48, 1998; Clapham, D. E. and Neer, E. J. G protein betagamma subunits. Annu.Rev.Pharmacol.Toxicol. 37:167–203, 1997; Hamm, H. E. and Gilchrist. A. Heterotrimeric G proteins. Curr. Opin.Cell Biol. 8:189–196, 1996).

This human GNB3 gene has been described by Levine et al. (Levine, M. A., Smallwood, P. M., Moen, P. T. Jr., Helman, L. J. and Ahn, T. G. Molecular cloning of β3 subunit, a third form of the G protein beta-subunit polypeptide. Proc.Natl.Acad.Sci. U.S.A. 87(6), 2329–2333 (1990)).

SUMMARY OF THE INVENTION

In one aspect of the invention provided is an isolated and purified nucleic acid sequence having the sequence set forth in SEQ ID NO:2.

In another aspect of the invention provided is method for diagnosing an increased likelihood of developing a disease associated with G protein dysregulation comprising determining the presence of a genetic modification in a gene obtained from a subject which encodes the Gbeta3 subunit of the human G protein, wherein the genetic modification is a substitution of cytosine by thymine at position 825 and/or 1429 of SEQ ID NO:2.

In yet another embodiment of the invention provided is a method for diagnosing an increased likelihood of a woman developing a cardiovascular condition, comprising determining the presence of a genetic modification in a G protein beta3 subunit obtained from the woman, wherein the genetic modification is a cystosine to thymine substitution of position 825 and/or 1429 of SEQ ID NO:2.

Further provided is a method for determining an increased risk of an individual for developing a disease associated with G protein dysregulation comprising comparing a gene sequence for the Gbeta3 subunit of the human G protein of the individual compares with a gene sequence of SEQ ID NO:2, wherein a correspondence between the sequences indicates an increased risk of disease being assigned to the individual.

In another aspect of the invention, provided is a method for determining an increased risk of an individual for developing a disease associated with G protein dysregulation comprising comparing a gene sequence for the Gbeta3 subunit of the human G protein of the individual compares with a gene sequence of SEQ ID NO:2, wherein a correspondence between the sequences indicates an increased risk of disease being assigned to the individual; and wherein to determine the risk of developing diabetes mellitus type 2, gene changes in the IRS1 gene (3931A variant; Gly971Arg), in the IRS2 gene, in the gene which codes for the p85 alpha regulatory subunit of P13 kinase (1020 G→A; codon 326 Met→Ile), in the gene which codes for the beta3 adrenergic receptor (Trp64Arg), in the gene which codes for the beta2-adrenergic receptor (here especially Arg16Gly variant and the Gln27Glu variant), in the gene which codes for the tumor necrosis factor alpha and/or in the gene which codes for leptine or the leptine receptor, are further evaluated.

In a related aspect of the invention, a method in accordance with the above is provided to determine the risk of developing obesity and adiposity, gene changes in the IRS1 gene (3931A variant; Gly971Arg), in the gene which codes for the beta3 adrenergic receptor (Trp64Arg variant), and/or in the gene which codes for the beta2-adrenergic receptor (here especially Arg16Gly variant and the Gln27Glu variant) are further evaluated.

In a further related aspect of the invention, a method is provided in accordance to determine the risk of developing coronary heart disease and/or myocardial infarction, gene changes in the IRS1 gene (3931A variant; Gly971Arg) are further evaluated.

In yet another aspect of the invention, provides is a method to determine the risk of developing diseases which are associated with increased reactivity of the immune system, wherein gene changes in the beta2-adrenergic receptor (here especially the Arg16Gly variant and the Gln27Glu variant) are further evaluated.

In related aspect of the invention a method is provided for determining the risk of an developing gestosis, wherein gene changes in the gene coding for endothelial NO synthase (especially the Glu298Asp variant) are further evaluated.

Also provided is the method as set forth above wherein an increased risk of developing AIDS is assigned to homozygotic HIV-positive individuals.

In a related aspect of the invention a method is provided to determine the risk of developing AIDS, wherein gene changes in the CCR5 gene are further evaluated and wherein a further increased risk of developing AIDS is assigned to the homozygotic or heterozygotic individuals for the CCR5_32 polymorphism.

Also provided is a method to determine the risk of developing AIDS, wherein gene changes in the CCR5 gene are further evaluated and wherein a further increased risk of developing AIDS is assigned to the individuals which carry the CCR5P1 allele.

Further, a method is provided to determine the risk of developing AIDS, wherein SDF1-3'UTR-801G-A polymorphism is evaluated and wherein a further increased risk of developing AIDS is assigned to the individuals which carry the SDF1-3'A allele.

In another embodiment of the invention, a method is provided for evaluating responsiveness of an individual to an in vivo pharmaceutical comprising evaluating the individual for a genetic modification in a gene encoding a Gbeta3 subunit of a protein, wherein the genetic modification is a substitution of cytosine by thymine at position 825 and/or at position 1429 of SEQ ID NO:2.

Another embodiment of the invention provides a method for evaluating responsiveness of an individual to in vivo to hormones, transmitters, neurotransmitters or pharmaceuticals which activate those G protein heterotrimers which contain the G protein subunits Gbeta3 and Gbeta3s and/or which stimulate the G protein subunit GalphaS comprising evaluating the individual for a genetic modification in a gene encoding a Gbeta3 subunit of a protein, wherein the genetic modification is a substitution of cytosine by thymine at position 825 and/or at position 1429 of SEQ ID NO:2.

Also provided is a method for evaluating responsiveness of an individual to treatment with beta-adrenoceptor blockers comprising evaluating the individual for a genetic modification in a gene encoding a Gbeta3 subunit of a human G protein, wherein the genetic modification is a substitution of cytosine by thymine position 825 and/or position 1429 of SEQ ID NO:2.

Further provided is a method for evaluating responsiveness of an individual in treatment with a substance having prostoglandin E1 action comprising evaluating the individual for a genetic modification in a gene enclosing a Gbeta3 subunit of a human G protein, wherein the genetic modification is a substitution of cytosine by thymine position 825 and/or position 1429 of SEQ ID NO:2.

In a related embodiment, use of a protein of the Gbeta3s subunit of the human G protein in recombined systems or after transfection in suitable cell lines is provided for identifying chemicals except for antibodies, which inhibit the function of Gbeta3s.

Also provided is a beta-3 subunit of a human G protein which has at most six WD repeat motives, wherein the Gbeta3s subunit has the amino acid sequence shown of SEQ ID NO:4.

Also provided is a nucleic acid sequence coding for a beta-3 subunit of a human G protein which has at most six WD repeat motives, wherein the Gbeta3s subunit has the amino acid sequence shown in SEQ ID NO:4; and wherein this nucleic acid sequence has the sequence of SEQ ID NO:4.

Further provided is a process for producing a beta-3 subunit of a human G protein which has at most six WD repeat motives wherein a nucleic acid sequence of the invention is introduced into a host and expressed; and this process wherein expression takes place in immune cells of immune-deficient animals, including HIV-positive patients.

Also provided is a use of a nucleic acid sequence for the beta-3 subunit of a human G protein which has at most six WD repeat motives, for producing a pharmaceutical for treatment of diseases which are associated with G protein dysregulation.

Further provided is a transgenic animal comprising the nucleic acid sequence nucleic acid sequence for the beta-3 subunit of a human G protein which has at most six WD repeat motives.

Also provided is n antibody directed against the protein comprising the beta-3 subunit of a human G protein which as at most six WD repeat motives, wherein the Gbeta3s subunit has the amino acid sequence shown of SEQ ID NO:4.

BRIEF DESCRIPTION OF THE DRAWINGS

FIG. 17 illustrates the β3 original sequence of Levine.

FIG. 18 shows SEQ ID. 2 with two polymorphisms.

FIG. 19 shows the nucleic acids sequence of cDNA of Gβ3 and a description of the deletion in Gβ3s and Gβ3s-2.

FIG. 20 shows SEQ ID NOS: 3 and 4, the nucleotide and amino-acid sequence, respectively, of Gβ3s-2.

DETAILED DESCRIPTION OF THE INVENTION

Figure 1:
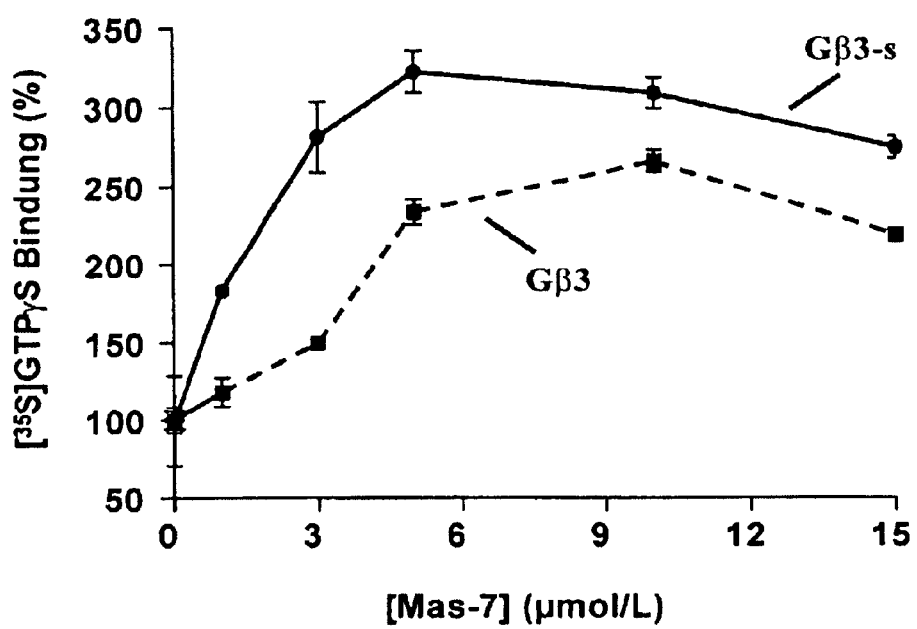
FIG. 1 illustrates the activation capacity of G proteins after transfection of Gβ3s using the COS-7 transfection system.

The subject matter of the invention is a novel human cDNA for the Gβ3 subunit of human G protein. It has been unexpectedly found that in the human GNB3 gene there is additional polymorphism which is called "C1429T" hereinafter. This polymorphism is located at position 1429 of the cDNA. This corresponds to exon 11 of the pre-mRNA, but outside the open read frame in the 3' untranslated area.

This polymorphism is in pronounced distribution equilibrium with the known C825T polymorphism such that almost all GBN3-825C alleles have the genotype 1429C and almost all GBN3-825T alleles have the genotype 1429T. Thus this polymorphism C1429T is just as well suited as polymorphism G825T for detection of increased activation capacity of G proteins.

The polymorphism C1429T is referenced to the cDNA sequence as was described by Levine et al. Here replacement of the C by a T takes place on position 1429 of the cDNA:

1381 ggcctgggtg gtatagggcg tttggccctg tgactatggc tctggcac (c/t)a ctagggtcct (SEQ ID NO: 5)

Referenced to the genomic sequence of the GBN3 locus as was described by Ansari-Lari et al (Ansari-Lari, M. A., Muzny, D. M., Lu, J., Lu. F., Lilley, C. E., Spanos, S., Malley, T. and Gibbs, R. A. A gene-rich cluster between the CD4 and triosephosphate isomerase genes at human chromosome 12p13. Genome Res. 6(4), 314–326 (1996)), this polymorphism is located as follows (C59308T):

59281 TTGGCCCTGT GACTATGGCT CTGGCAC(C/T) AC TAGGGTCCTG GCCCTCTTCT TATTCATGCT (SEQ ID NO: 6)

The complete genomic sequence is listed as SEQ ID 2.

This polymorphism is detected using methods which are familiar to one skilled in the art, such as specific hybridization, sequencing, PCR reaction with subsequent restriction analysis, DNA chip technology, single strand conformation polymorphism, etc. In one sample experiment detection was done by amplification of the corresponding gene section and subsequent analysis of the restriction fragment length polymorphism in which the restriction enzymes BanI, BshNI, Eco641 or their isoschizomers are used.

As a result there is good agreement between the genotype on positions 825 and 1429:

TABLE I

| Genotype on position 825 of GNB3 cDNA | Genotype TT at position 1429 of cDNA | Genotype TC at position 1429 of cDNA | Genotype CC at position 1429 of DNA |
|---|---|---|---|
| TT 119 | 111 (93.3%) | 8 (6.7%) | 0 |
| TC 116 | 3 (2.6%) | 103 (88.8%) | 10 (8.6%) |
| CC 124 | 0 (0%) | 2 (1.6%) | 122 (98.4%) |

The new nucleic acid sequence can be used to produce antisense drugs for treatment or prevention of diseases, one nucleic acid sequence which is complementary nucleic acid sequence being used to produce the antisense drug. Here patients can be treated for example with antisense oligonucleotides or vectors for prevention of transcription or translation of the Gβ3 subunit.

The subject matter of the invention is furthermore the use of β3 subunits of G proteins for determining the risk of developing a disease which is associated with G protein dysregulation.

Although the Gβ3s splice variant which has polymorphism C1429T or which can be attributed to polymorphism C825T, in combination with the G protein subunits Galphai2 and Ggamma5, can form a functional heterotrimer, it was unclear how Gβ3s leads to increased activation capacity of the G proteins.

The subject matter of this invention is based on the finding that the Gβ3s subunit leads to increased activation capacity of G proteins. The increased activation capacity of G proteins was detected via transfection of the corresponding cDNAs and the expression of Gβ3 and Gβ3s in the COS-7 transfection system which is well known to one skilled in the art. Here it was found that the activation capacity of G proteins after transfection of Gβ3s is clearly increased compared to Gβ3 (FIG. 1). To quantify the activation capacity of G proteins, here the incorporation of radioactively tagged [35S]GTPgammaS into G protein alpha-subunits after stimulation with the peptide mastoparan-7 (Mas-7) was measured.

Figure 2:
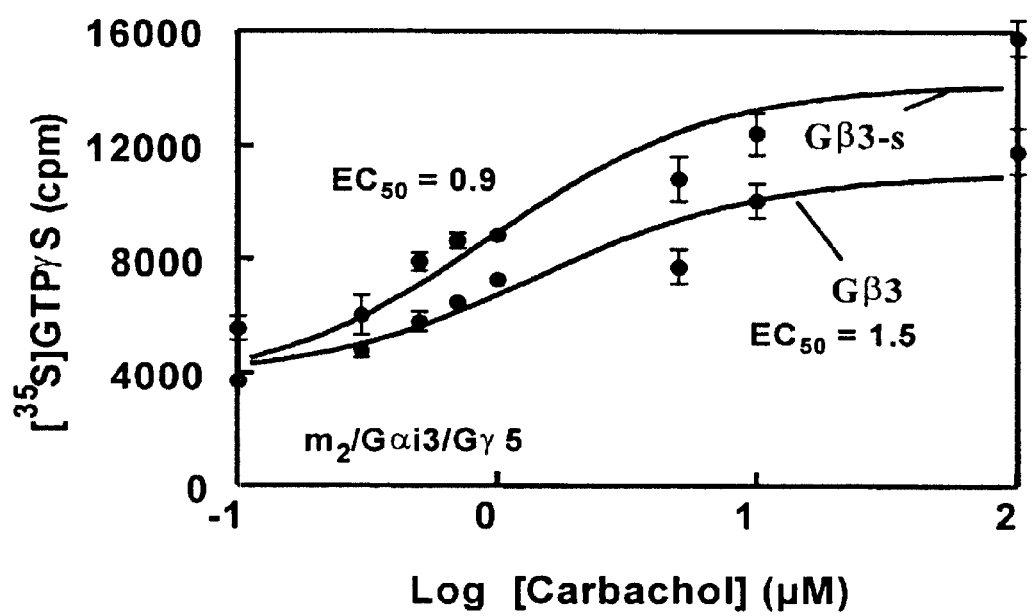
FIG. 2 illustrates the increased potency and increased efficiency of the agonist carbachol with reference to the stimulation capacity of G proteins using the Sf9 system.

Similar results can be achieved in the Sf9 insect cells expression system (FIG. 2). Here the m2-muscarinergic receptor is expressed together with the G protein subunits Galphai3 and Ggamma5 and either Gβ3 or Gbeta3-s in the Sf9 system. After stimulation with the agonist carbachol, in the presence of Gβ3, increased potency and increased efficiency of the agonist carbachol were observed with reference to the stimulation capacity of G proteins.

These experiments show that the splice variant Gβ3-s is originally responsible for increased activation of G proteins. Furthermore these experiments prove that the protein is suitable for gene therapy for diseases which are associated with one such G-protein dysregulation for purposes of achieving increased cellular reactivity.

The diseases which are associated with G protein dysregulation are defined as those diseases in which the G protein is involved in signal transduction and does not perform its function physiologically. The dysregulation can have a series of causes, for example a change in the structure gene or an altered gene expression. This invention relates to diseases which are associated with the above described GNB3-825T allele or GNB3-1429 allele. They include diabetes mellitus (type 2), obesity and adiposity, coronary heart disease, immune diseases as a result of the intensified function of the immune system, and risky pregnancies with the danger of premature birth.

The following example relates to studies with the GNB3-825T allele. As a result of the extensive agreement (coupling equilibrium) between the genotype at positions 825 and 1429 these examples and the conclusions drawn from the experimental results are likewise valid for the GNB3-1429T allele.

1. Prediction of Diabetes Mellitus (Type 2)

Type-2 diabetes (synonyms: adult diabetes, non-insulin dependent diabetes) is a serious disease with high cardiovascular morbidity and mortality. Genetic influences and obesity contribute heavily to the pathogenesis. Type-2 diabetes often begins as insulin resistance which is first compensated by increased insulin secretion so that the affected individuals remain without symptoms (euglycemic). Only when the increased insulin secretion can no longer be maintained does diabetes with increased blood sugar levels occur. On the cellular level changes in components of insulin signal transduction, for example in the insulin receptor substrate 1 (IRS-1), PT-3 kinases, protein kinases, etc., can cause insulin resistance. But also after cell stimulation with agonists (for example, angiotensin II) which activate the G protein-coupled receptors can cellular insulin resistance be caused. The action of subsequent stimulation with insulin is then clearly reduced (Polonsky, K. S., Sturis, J., and Bell, G. I. Non-insulin dependent diabetes mellitus—A genetically programmed failure of the beta cell to compensate for insulin resistance. N. Engl. J. Med. 334:777–783, 1996; O'Doherty, R. Stein, D. and Foley, J. Insulin resistance. Diabetologia 40 Suppl 3:B 10–5:B 10–5, 1997; Kahn, C. R., Vicent, D., and Doria, A. Genetics of non-insulin dependent (type-II) diabetes mellitus. Annu. Rev. Med. 47:509–531, 1996; Hansen, T., Andersen, C. B., Echwald, S. M., Urhammer, S. A., Clausen, J. O., Vestergaard, H., Owens, D., Hansen, L. and Pedersen, O. Identification of a common amino acid polymorphism in the p85alpha regulatory subunit of phosphatidylinositol 3-kinase: effects on glucose disappearance constant, glucose effectiveness, and the insulin sensitivity index. Diabetes 46(3): 494–501, 1997; Folli, F., Kahn, C. R., Hansen, H., Bouchie, J. L. and Feener, E. P. Angiotensin II inhibits insulin signalling in aortic smooth muscle at multiple levels—A potential role for serine phosphorylation in insulin/angiotensin crosstalk. J. Clin. Invest. 100:2158–2169, 1997; Zhang, Y., Wat, N., Stratton, I. M., Warren-Perry, M. G., Orho, M., Groop, L. and Turner, R. C. UKPDS 19: heterogeneity in NIDDM: separate contributions of IRS-1 and b3-adrenergic receptor mutations to insulin resistance and obesity respectively with no evidence for glycogen synthase gene mutations. Diabetologia 39:1505–1511, 1996; Alming, K., Bjorbaek, C., Vestergaard, H., Hansen, T., Echwald, S. and Pedersen, O. Aminoacid polymorphisms of insulin receptor substrate-1 in non-insulin-dependent diabetes mellitus. Lancet 342:828–832, 1993; Laakso, M., Malkki, M., Kekalainen, P., Kuusisto, J., and Deeb, S. S. Insulin receptor substrate-1 variants in non-insulin dependent diabetes. J. Clin. Invest. 94: 1141–1146, 1994).

This G protein activation leads to phosphorylation of IRS-1 on serine residues, by which the phosphorylation induced by insulin on tyrosine residues is reduced. As a result a reduced interaction of IRS-1 occurs with the insulin receptor and the PI-3 kinase, i.e. reduced insulin action. An increased activation capacity of the G proteins which is caused by the GNB3 825T allele and the associated splice variant Gβ3-s in vivo clearly intensifies the tendency to insulin resistance.

It has now been shown that with the simultaneous presence of mutations in components of insulin signal transduction (IRS1 gene, 3931A variant, Gly971Arg, p85 alpha regulatory subunit of PI3 kinase (1020 G→A; codon 326 Met→Ile; β3 adrenergic receptor (Trp64Arg); β2-adrenergic receptor (here especially Arg16Gly variant and the Gln27Glu variant); tumor necrosis factor alpha; leptine or the leptine receptor) which lead to insulin resistance, and the GNB3-825T allele, the tendency to insulin resistance and to diabetes rises drastically. This connection opens the possibility of diagnosis of a type-2 diabetes mellitus associated with the GNB3-825T allele and prediction of one such genetically induced tendency to type-2 diabetes mellitus in still healthy individuals without complaints.

The DNA from more than 700 patients with type-2 diabetes and from 1400 healthy controls was obtained for proof. The frequencies of the GNB3-825T allele and the IRS-1-Gly971Arg variant were compared.

Table II shows first of all a comparison of the allele frequencies in controls and cases:

Values correspond to n (%) for alleles and diabetes-associated diseases and averages (SD) for continuous variables.[1], $p<0.02$ ($chi^2=8.1$) versus control females; [2], $p<0.001$ ($chi^2=14.4$) versus all controls; [3], $p<0.001$ ($chi^2=20.0$) versus control males; [4], $p<0.005$ ($chi^2=12.9$) versus all controls; [5], $p<0.01$ ($chi^2=13.2$) versus control males; [6], $p<0.14$ ($chi^2=3.1$) versus control females.

TABLE II

ALLELE FREQUENCIES IN CONTROLS AND TYPE 2 DIABETICS

|  |  | Controls | | | Diabetics | | |
|---|---|---|---|---|---|---|---|
|  |  | All | Men | Women | All | Men | Women |
| Total, n |  | 1464 | 962 | 502 | 720 | 320 | 400 |
| Genotype, n (%): |  |  |  |  |  |  |  |
| GNB3 | TT | 116 (8) | 83 (9) | 33 (7) | 61 (8) | 32 (10) | 29 (7) |
|  | TC | 585 (40) | 360 (37) | 225 (45) | 345 (48) | 161 (50) | 184 (46) |
|  | CC | 763 (52) | 519 (54) | 244 (49) | 314 (44) | 127 (40) | 187 (47) |
|  | FT | 0.28 | 0.27[1] | 0.29 | 0.32[2] | 0.35[3] | 0.30 |
| IRS1 | AA | 5 (0) | 4 (0) | 1 (0) | 8 (1) | 4 (1) | 4 (1) |
|  | AG | 159 (11) | 108 (11) | 51 (10) | 108 (15) | 58 (18) | 50 (13) |
|  | GG | 1300 (89) | 850 (88) | 450 (90) | 604 (84) | 258 (81) | 346 (87) |
|  | FA | 0.06 | 0.06 | 0.05 | 0.09[4] | 0.10[5] | 0.07[6] |
| Age (SD) |  | 49 (10) | 48 (10) | 50 (9) | 63 (9) | 62 (9) | 64 (9) |
| Age when diagnosed (SD) |  |  |  |  | 46 (10) | 45 (10) | 47 (10) |
| BMI, kg/m$^2$ (SD) |  | 26.9 (3.9) | 27.0 (3.4) | 26.3 (4.8) | 28.9 (4.8) | 28.4 (44)[6] | 29.3 (5.0) |
| Nephropathy, n (%) |  |  |  |  | 198 (31) | 105 (36) | 93 (28) |
| Hypertension, n (%) |  |  |  |  | 464 (67) | 181 (59) | 283 (73) |

The following tables III and IV show the risk for carriers of the GNB3-825T allele or carriers of the IRS-3931A allele (simple effects, Table III) or for carriers of both alleles (combined effects Table IV) for developing type-2 diabetes. The risk here is expressed as an age-adjusted odds ratio, the odds ratio for the case-control studies corresponding roughly to the relative risk in prospective studies.

TABLE III

Odds ratios for diabetes for carriers of the GNB3-T825 allele, the IRS-A-3931 allele or both alleles.
Age-adjusted odds ratios are shown.
Single Effects

|  |  | All | | | | Men | | | | Women | | | |
|---|---|---|---|---|---|---|---|---|---|---|---|---|---|
| Genes | Allele | Control (n) | Diab. (n) | OR (95% CI) | p-value | Control (n) | Diab. (n) | OR (95% CI) | p-value | Control (n) | Diab. (n) | OR (95% CI) | p-value |
| GNB3 | TT/CC | 116 / 763 | 61 / 314 | 1.25 (0.81–1.92) | 0.3180 | 83/519 | 32/127 | 1.44 (0.83–2.51) | 0.2002 | 33/244 | 29/187 | 1.22 (0.60–2.46) | 0.5882 |
| GNB3 | TC/CC | 585 / 763 | 345 / 314 | 1.48 (1.17–1.87) | 0.0011 | 360 / 519 | 161 / 127 | 1.86 (1.35–2.57) | 0.0002 | 225 / 244 | 184 / 187 | 1.12 (0.79–1.58) | 0.5351 |
| GNB3 | TT + TC/CC | 701 / 763 | 406 / 314 | 1.44 (1.15–1.80) | 0.0015 | 443 / 519 | 193 / 127 | 1.78 (1.31–2.43) | 0.003 | 258 / 244 | 213 / 187 | 1.13 (0.80–1.58) | 0.4834 |
| IRS1 | AA/GG | 5/1300 | 8/604 | 2.26 (0.53–9.59) | 0.2686 | 4/850 | 4/285 | 1.71 (0.32–9.12) | 0.5300 | 1/450 | 4/346 | 6.74 (0.42–109.57) | 0.1797 |
| IRS1 | AG/GG | 59 / 1300 | 108 / 604 | 1.35 (0.97–1.89) | 0.0802 | 108 / 850 | 58/258 | 1.76 (1.14–2.69) | 0.0100 | 51/450 | 50/346 | 0.99 (0.57–1.72) | 0.9762 |
| IRS1 | AA + AG/GG | 164 / 1300 | 116 / 604 | 1.38 (1.00–1.92) | 0.0531 | 112 / 850 | 62/258 | 1.75 (1.15–2.67) | 0.0086 | 52/450 | 54/346 | 1.07 (0.62–1.83) | 0.8122 |

TABLE IV

Odds ratios for diabetes for carriers of the GNB3-T825 allele, the IRS-A-3931 allele or both alleles.
Age-adjusted odds ratios are shown.
Combined Effects

| Genes | Allele | All | | | | Men | | | | Women | | | |
|---|---|---|---|---|---|---|---|---|---|---|---|---|---|
| | | Control (n) | DIAB. (n) | OR (95% CI) | p-value | Control (n) | DIAB. (n) | OR (95% CI) | p-value | Control (n) | DIAB. (n) | OR (95% CI) | p-value |
| GNB3 (IRS1 GG) | TT/CC | 106 / 684 | 50/264 | 1.13 (0.70– 1.81) | 0.6156 | 75/461 | 25/104 | 1.31 (0.71– 2.42) | 0.3926 | 31/223 | 25/160 | 1.09 (0.52– 2.32) | 0.8157 |
| GNB3 (IRS1 GG) | TC/CC | 510 / 684 | 290 / 264 | 1.53 (1.19– 1.96) | 0.0010 | 314 / 461 | 129 / 104 | 1.90 (1.33– 2.70) | 0.0004 | 196 / 223 | 161 / 160 | 1.19 (0.82– 1.72) | 0.3600 |
| GNB3 (IRS1 GG) | TT + TC/ CC | 616/ 684 | 340 / 264 | 1.46 (1.15– 1.86) | 0.0022 | 389 / 461 | 154 / 104 | 1.78 (1.27– 2.50) | 0.0008 | 227 / 223 | 186 / 160 | 1.18 (0.82– 1.68) | 0.3743 |
| IRS1 (GNB3 CC) | AA + AG/GG | 79/684 | 50/264 | 1.48 (0.90– 2.43) | 0.1198 | 58/461 | 23/104 | 1.78 (0.93– 3.38) | 0.0782 | 21/223 | 27/160 | 1.33 (0.59– 3.00) | 0.4984 |
| IRS1 + GNB3 | TT + AA or AG/CC GG | 10/684 | 11/264 | 3.38 (1.13– 10.08) | 0.0291 | 8/461 | 7/104 | 4.03 (1.12– 14.56) | 0.0333 | 2/223 | 4/160 | 3.39 (0.49– 31.60) | 0.1975 |
| IRS1 + (GNB3) | TC + AA or AG/CC GG | 75/684 | 55/264 | 1.69 (1.05– 2.73) | 0.0311 | 43/461 | 32/104 | 2.82 (1.52– 5.23) | 0.0010 | 28/223 | 23/160 | 0.89 (0.41– 1.93) | 0.7706 |
| IRS1 + GNB3 | TC or TT + AA or AG/ CC + GG | 85/684 | 66/264 | 1.87 (1.19– 2.92) | 0.0062 | 54/461 | 39/104 | 2.99 (1.69– 5.30) | 0.0002 | 31/223 | 27/160 | 1.05 (0.51– 2.17) | 0.8959 |

A clear risk increase for type-2 diabetes for carriers of the GNB3-825T allele or carriers of the IRS-3931A allele (Tables III and IV) is apparent. A drastic risk increase can be found in individuals in whom both genes are changed. Thus the detection of the GNB3-825T allele can be used to ascertain in the affected individual the tendency to develop type-2 diabetes or to determine a genetically induced cause of a condition which has already occurred.

2. Prediction of Adiposity/Obesity

The regulation of the body mass index (BMI), a measure of the ratio of body weight to body size, is determined by many genes. Obesity is up to roughly 40% genetically determined, but is also caused by excess calorie intake with existing lack of exercise. The Gβ3-s splice version is associated with the cellular phenotype of increased cell growth. Thus it is also possible that the GNB3-825T allele predisposes to increased body growth, among others obesity, and can exert epistatic and hypostatic effects. In doing so, as in diabetes mellitus (type 2) there can be a relationship to changes in the IRS1 gene (3931A variant; Gly971Arg), in the gene which codes for the β3 adrenergic receptor (Trp64Arg variant) and in the gene which codes for the β2 adrenergic receptor, here especially the Arg16Gly variant and the Gln27Glu variant.

Studies on transgenic mice have shown that the lack of the gene which codes for the IRS-1 protein in contrast leads to a serious delay of body growth (Tamemoto, H., Kaowaki, T., Tobe, K., Yagi, T., Sakura, H., Hayakawa, T., Terauchi, Y., Ueki, K., Kaburagi, Y., Satoh, S., Sekihara, H., Yoshioka, S., Horikoshi, H., Furuta, Y., Ikawa, Y., Kasuga, M., Yazaki, Y., and Aizawa, S. Insulin resistance and growth retardation in mice lacking insulin receptor substrate-1. Nature 372: 182–186, 1994).

In order to check the correlation of adiposity with the presence of the GNB3-825 nucleotide and the status of the IRS1 gene with respect to the presence of the Gly971Arg variant, the BMI was measured in 20–30 year old healthy males in whom at the same time the status of the GNB3-825 nucleotide and the status of the IRS1 gene were studied with respect to the presence of the Gly971Arg variant.

Figure 3:
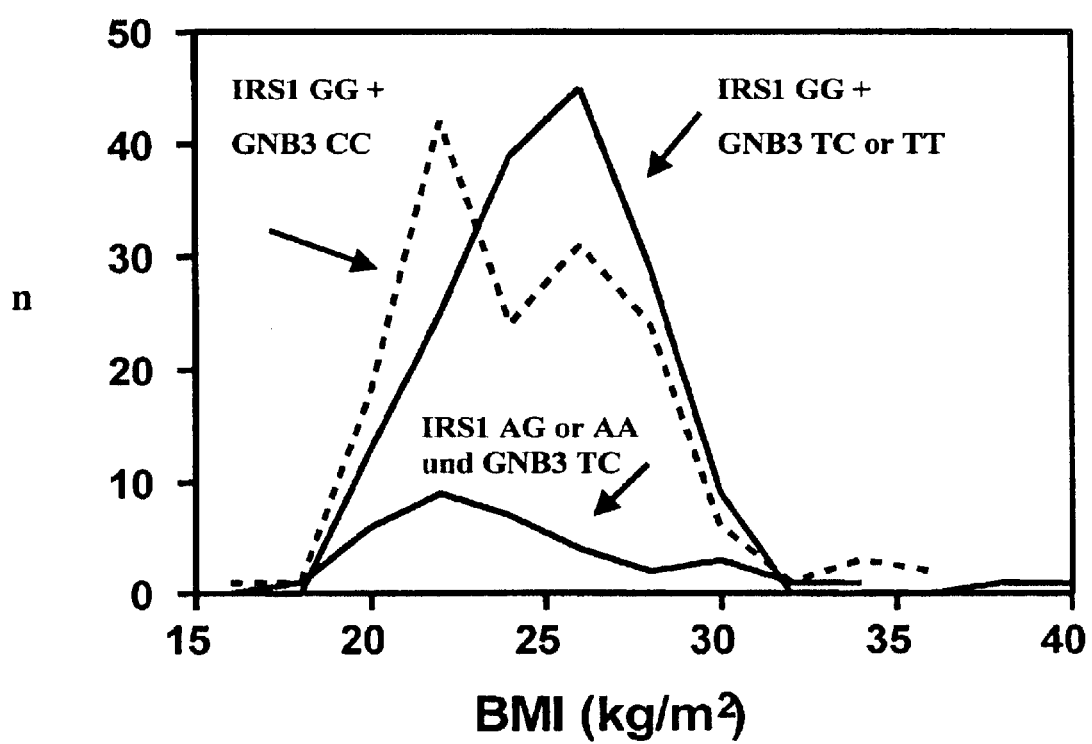
FIG. 3 illustrates the frequency distribution of the measured values for the BMI.

FIG. 3 shows the frequency distribution of the measured values for the BMI. In the presence of the more frequent IRS1 "GG" genotype a significant tendency to increased BMI can be detected with the GNB3-825T allele compared to the GNB-C825 allele. The odds ratio for the 75% quartile compared to the 25% quartile is 2.5. Conversely, the tendency to increased BMI in carriers of the GNB3-825T allele with the simultaneous presence of the IRS1-3931A allele (Gly971Arg variant) is clearly counteracted. This illustrates the interactive effect of GNB3 and IRS1 on the BMI. Thus, the presence of the GNB3-825T allele can reliably correlate with adiposity. It is therefore possible to predict a tendency to adiposity in carriers of this allele, especially those in whom at the same time the IRS1-3931A allele (Gly971Arg variant) is lacking.

825T allele carriers, as is described for example in DE 196 19 362 A1, have an increased risk of developing hypertension. Since obesity and adiposity predispose to a very high degree to cardiovascular conditions, it was studied whether young people with normal blood pressure who carry a 825T allele already have an increased risk for obesity and adiposity. To do this, in 277 young normotensive males the body size and body weight were determined and the blood pressure measured. Obesity is defined as a BMI ˆ $25.0 \, kg/m^2$ and adiposity as ˆ $27.0 \, kg/m^2$. There is a clear relationship between the BMI and the blood pressure values. The frequency of the 825T allele increases linearly from the 1st to the 4th BMI quartile. For homozygotic 825T allele carriers the following risks (odds ratios; OR) can be computed a) BMI ˆ 25.0 kg/m² versus BMI<25 kg/m² (obesity versus normal weight): OR TT/CC=2.5 (1.1–6.1; p=0.03); OR TC/CC 1.5 (0.8–2.6; p=0.2)

b) BMI ˆ 27 kg/m² versus BMI<25 kg/m² (adiposity versus normal weight): OR TT/CC=5.0 (1.4–18.3; p=0.0083); OR TC/CC 2.2 (0.8–6.3; p=0.13)

Thus, a clear relationship arises between the presence of a 825T allele and the tendency to obesity and adiposity. This explains among others to some extent the increased risk of 825T allele carriers for hypercholesteremia, diabetes, hypertension, and coronary heart disease/myocardial infarction.

TABLE V

GNB3 825T allele, BMI and bloodpressure values Genotypes are given as n % and continuous variables as averages (standard deviation); fT = 825T allele frequency; BMI (body mass index) is given as kg/m². BP syst-systolic blood pressure; BP diast-diastolic blood pressure.

| | | BMI Quartile | | | | |
|---|---|---|---|---|---|---|
| GNB3 | All | 1 <21.7 | 2 21.7– 23.4 | 3 23.4– 25.0 | 4 ≧25.0 | >27 kg/m2 |
| TT | 28 (10) | 2 (3) | 6 (8) | 9 (13) | 11 (16) | 5 (23) |
| TC | 121 (44) | 27 (39) | 27 (40) | 34 (49) | 33 (47) | 11 (50) |
| CC | 128 (46) | 40 (58) | 36 (52) | 26 (38) | 26 (37) | 6 (27) |
| Σ | 277 | 69 | 69 | 69 | 70 | 22 |
| fT (%) | 31.9 | 22.5 | 28.3 | 37.7 | 39.3 | 47.7 |
| Age (years) | 25.6 (3.4) | 24.8 (3.6) | 25.6 (3.2) | 25.3 (3.4) | 26.4 (2.9) | 26.5 (2.9) |
| Size (cm) | 180.4 (7.3) | 180.8 (6.4) | 180.5 (7.4) | 180.7 (7.1) | 179.6 (7.4) | 181.0 (5.9) |
| Weight (kg) | 76.5 (9.8) | 67.4 (5.2) | 73.1 (6.3) | 78.9 (7.1) | 86.2 (8.7) | 93.5 (6.9) |
| BP syst (mm Hg) | 129.8 (11.1) | 126.3 (9.1) | 130.2 (9.4) | 130 (11.8) | 133 (12.9) | 135.9 (10.7) |
| BP diast (mm Hg) | 79.1 (7.9) | 75.8 (7.9) | 79.4 (5.5) | 79.7 (7.3) | 81.9 (9.2) | 84.3 (9.8) |

3. Prediction of Coronary Heart Disease and Atherosclerosis

It is already known that coronary heart disease can be associated with a G protein dysregulation. In order to verify a relationship between the occurrence of coronary heart disease and the presence of the GNB3-825T allele, patients with angiographically precluded coronary heart disease, with coronary heart disease (without myocardial infarction), with myocardial infarction and with more than one myocardial infarction were checked for the presence of this allele. The result is shown in FIG. 4.

Figure 4:
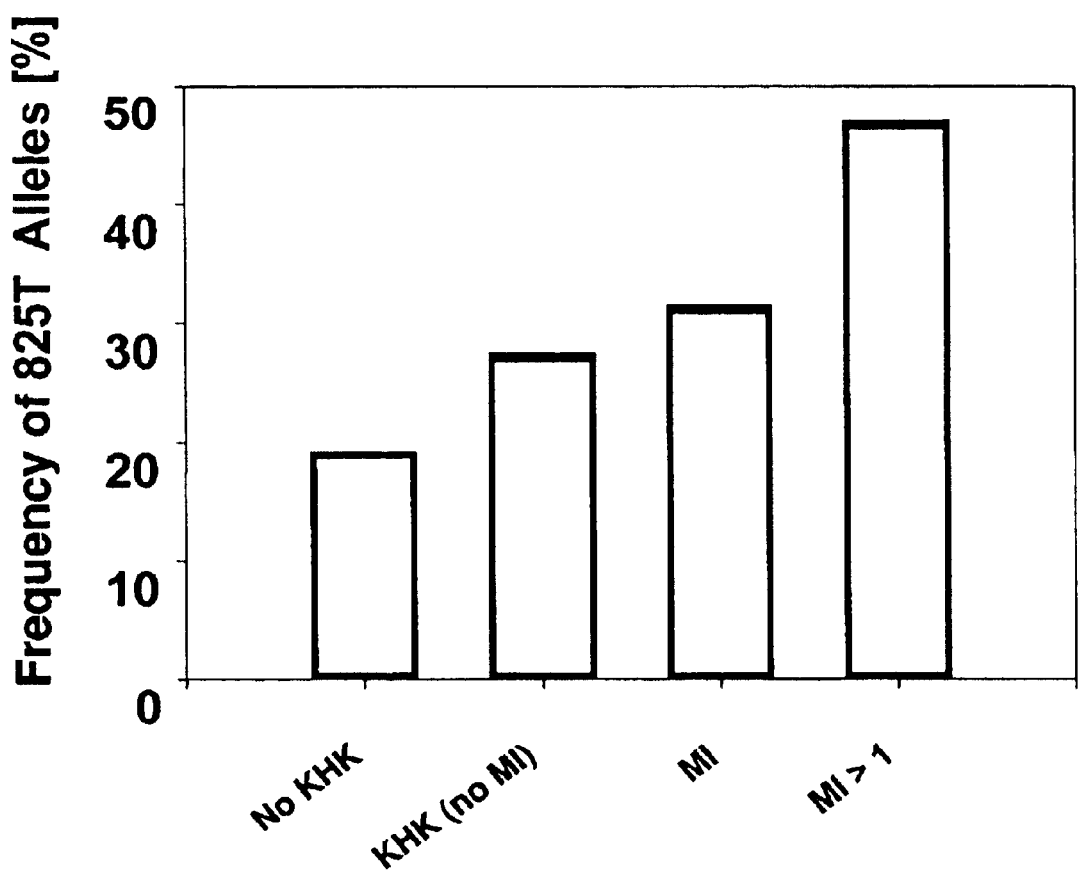
FIG. 4 illustrates the frequency of the GNB3-825T allele in patients with angiographically precluded coronary heart disease (CHD), with (CHD) (without myocardial infarction; MI), with myocardial infarction MI and with more than one myocardial infarction.

FIG. 4 shows the frequency of the GNB3-825T allele in patients with angiographically precluded coronary heart disease (CHD), with (CHD) (without myocardial infarction; MI), with myocardial infarction MI and with more than one myocardial infarction.

A clear rise is apparent in the frequency of the GNB3-825T allele in CHD and MI. The risk for CHD and MI is roughly doubled by the GNB3-825T allele compared to controls without CHD.

Patients with mutation in the IRS-1 protein (3931A allele; Gly971Arg variant) however experience a clear risk reduction by up to 50% in the presence of the GNB3-825 allele or GNB3-825T allele. This change in the IRS-1 protein therefore exerts hypostatic effects, i.e. this variant protects against coronary heart disease.

If we compare patients with CHD to individuals with coronary-angiographically precluded CHD, the odds ratios are as follows:

TABLE VI

| KHK positive GNB3 + IRS1-Status | KHK negative GNB3 + IRS1-Status | OR | P-value |
|---|---|---|---|
| TT/TC + AG/AA | TT/TC + GG | 0.94 | Not significant |
| TT/TC + GG | CC + GG | 1.4 | 0.003 |
| TT/TC + GG | CC + AG/AA | 2.8 | 0.002 |

Thus the correlation between the presence of the GNB3-825T allele and the occurrence of coronary heart disease is proven. Thus it is possible to predict a tendency to coronary heart disease in carriers of this allele, especially those in whom the IRS1-3931A allele (Gly971Arg variant) is lacking.

One special application is the prediction of a coronary heart disease, but also in general of the cardiovascular risk (high blood pressure, etc.) in women with the objective of administering to them controlled, post-menopausal hormone therapy with the female sex hormone in order to reduce cardiovascular risk.

Another application is the prediction of increased risk for myocardial infarctions and sudden cardiac death. This is associated among others with G proteins also controlling ion channels. More accurately, the Galpha and Gbetagamma subunits of G proteins control the function of diverse ion channels, for example $Na^+$ channels, $Ca^{2+}$ channels and $K^+$ channels. More accurately matched regulation of these ion channels is of great importance for all electrically excitable tissues, especially for the heart (De Waard, M., Liu, H., Walker, D., Scott, V. E., Gurnett, C. A. and Campbell, K. P. Direct binding of G protein betagamma complex to voltage-dependent calcium channels. Nature 385 (6615): 446–450, 1997; Ma, J. Y., Catterall, W. A., and Scheuer, T. Persistent sodium current through brain sodium channels induced by G protein betagamma subunits. Neuron 19(2),: 443–452, 1997; Kofuji P., Davidson, N. and Lester, H. A. Evidence that neuronal G-protein-gated inwardly rectifying $K^+$ channels are activated by Gbetagamma subunits and function of heteromultimers. Proc.Natl.Acad.Sci.USA 92: 6542–6546, 1995; Krapivinksy, G., Krapivinsky, L., Wickman, K., and Clapham, D. E. Gbetagamma binds directly to the G protein-gated $K^+$ channel, $I_{KACh}$, J. Biol. Chem. 270:29059–29062, 1995).

It has been found that individuals carrying the GNB3-T825 allele have intensified activity of myocardial $K^+$ channels. This leads to accelerated repolarization of the cardiac muscle cell and thus to shortened refractory time. These individuals are thus subject to increased risk for cardiac irregularities, especially ventricular tachycardias, extrasystoles, ventricular flutter and ventricular fibrillation. They bear an increased risk for sudden cardiac death also within the framework of acute myocardial infarction.

Finally, carriers of the GNB3-825T allele already at an age from 20 to 30 show clear changes of the properties of the blood vessels. Especially conspicuous are an increased pulse rate, increased cardiac output and increased pulse pressure. These phenomena express an early-onset tendency to increased stiffness of the blood vessels (reduced compliance) as an indicator for atherosclerosis. Genotyping to ascertain the GNB3-825T allele status is thus suited to ascertaining an increased risk of atherosclerosis.

4. Prediction of an Increased Cholesterol Concentration in the Blood

It is generally known that individuals with an increased concentration of total cholesterol in the blood can be assigned an increased risk for coronary heart disease and cardiac infarction. A total 232 individuals aged from 18 to 40 years were genotyped with reference to the C825T polymorphism in GNB3 and the total cholesterol in the serum was quantified using standard methods. Subsequently the measured cholesterol concentrations (mg/dl) were divided into quartiles, and the genotype on the GNB3 locus was assigned to the quartiles. The lowest frequency of the 825T allele is found with 23.3% in the 1st quartile, while the frequencies of the 825T allele in quartiles 2–4 is clearly higher. These results are depicted in Table VI.

TABLE VII

| | Cholesterol Concentration | | | |
|---|---|---|---|---|
| | 1. Quartile −163 mg/dl | 2. Quartile −181 mg/dl | 3. Quartile −212 mg/dl | 4. Quartile >212 mg/dl |
| TT | 4 (9) | 4 (8) | 12 (17) | 7 (12) |
| TC | 13 (29) | 21 (44) | 32 (46) | 28 (47) |
| CC | 28 (62) | 23 (48) | 26 (37) | 24 (41) |
| ft | 23.3% | 30.2% | 40.0% | 35.6% |

The numbers correspond to n (%)

If the genotype distribution above the median value (>181 mg/dl; TT=19; TC=60; CC=50; frequency of the 825T allele: 38%) is compared to that below the median value ('181 mg/dl; TT=8; TC=34; CC=51; frequency of the 825T allele: 26.9%), the risks for cholesterol values in the range above the median are as follows: Odds ratio TT/CC=2.4 (p=0.053); odds ratios TC/CC=1.8 (p<0.05)

Thus the 825T allele is associated with an increased risk for hypercholesterolemia.

Genotyping on the GNB3 locus therefore offers the possibility for ascertaining an increased risk for hypercholesterolemia with the objective of treating the affected individuals with drugs which can reduce the elevated cholesterol. They include especially inhibitors of the enzyme 3-hydroxy-3-methyl-glutaryl-coenzyme A reductase (HMG-CoA reductase), for example simvastatin, pravastatin, fluvastatin, lovastatin, atorvastatin and other so-called "statins". They also include sitosterine, sitostanol ester (also in foods), fibrates and other substances which reduce cholesterol.

These drugs act as G protein inhibitors and can thus be used therapeutically in diseases which are associated with G protein dysregulation.

5. Prediction of Increased Immune System Function

G proteins and G protein-coupled receptors are also found in all cells of the immune system, especially also in leukocytes. Chemotaxis of cells is mediated mainly by betagamma subunits of heterotrimeric G proteins. Thus the GNB3-825T allele should lead to increased reactivity of the immune system, especially to intensified immune defense.

Figure 5:
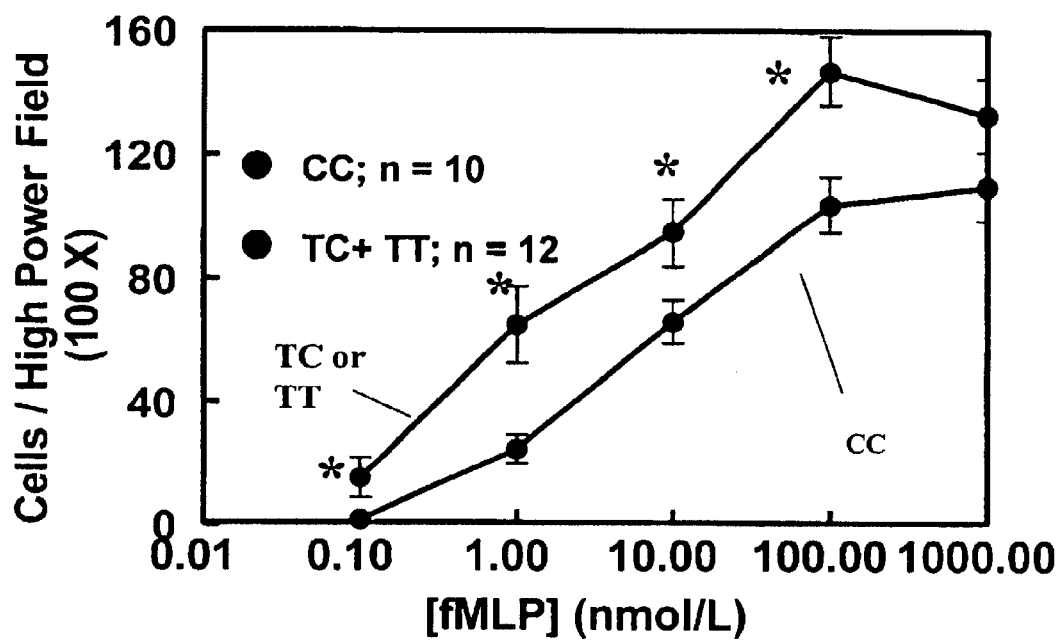
FIG. 5 illustrates the increased reactivity of the immune system as result of the GNB3-825T allele.

In fact, neutrophilic granulocytes of carriers of the GNB3-825T allele have increased chemotaxis compared to the peptide fMLP (FIG. 5). fMLP is a peptide which is representative of a host of bacterial peptides and which stimulates chemotactic reactions. It is therefore used as a test system for measurement of chemotactic reactions of cells which is well known to one skilled in the art. The fMLP receptor, as is known, activates the pertussis toxin-sensitive G proteins. The statement that granulocytes of carriers of the GNB3-825T allele show intensified fMLP-stimulated chemotaxis is in agreement with the fact that chemotaxis of betagamma subunits is mediated.

This phenomenon can also be detected in other leukocytes as well, for example, lymphocytes. Thus there is a correlation between the GNB3-825T allele and increased chemotaxis of cells of the immune system, for example neutrophilic granulocytes, T lymphocytes, see also 6., or B lymphocytes.

Furthermore, in carriers of the GNB3-825T allele an increased tendency toward proliferation of cells of the immune system, especially also after inoculations, is observed.

Figure 6:
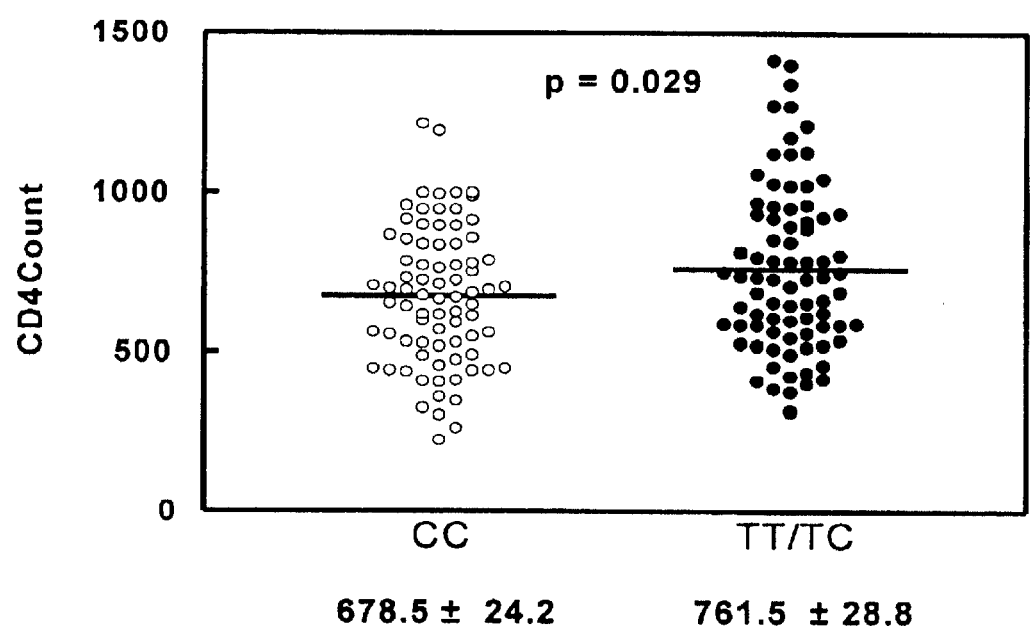
FIG. 6 illustrates an increased number of CD4 lymphocytes in healthy carriers of the GNB3-825T allele show an increased number of leukocytes and CD4-positive T lymphocytes (absolute and percentage) with an increased CD4/CD8 quotient.

Healthy carriers of the GNB3-825T allele show an increased number of leukocytes and CD4-positive T lymphocytes (absolute and percentage) with an increased CD4/CD8 quotient. FIG. 6 shows this for an increased number of CD4 lymphocytes. Conversely, carriers of the GNB3-825T allele also show an increased tendency to developing AIDSs after a HIV infection, see also 7., also in conjunction with the detection of the aforementioned gene change in chemokine receptors, especially a __32 deletion in the CCR5 receptor or in the area of the promotor of this gene.

Finally, among affected individuals, increased release of immune-modulator substances, hormones and other substances from leukocytes is observed (cytokines, interleukins, growth factors, antibodies, vaso-active substances). In this connection intensified immune defense also arises after transplantation of organs or tissues (kidneys, heart, bone marrow, lungs, skin, liver, etc.) with the danger of transplant rejection. In addition, this results in an increased tendency to autoimmune conditions (rheumatism, ulcerative colitis, Crohn's disease) and to allergic conditions, for example, of the skin, the respiratory passages or other organs (for example, neurodermatitis, hay fever, bronchial asthma). This is also observed in combination with the detection of other gene changes, for example in the β2-adrenergic receptor, here especially the Arg16Gly variant and the Gln27Glu variant.

6. Prediction of Increased T Lymphocyte Function

Figure 7:
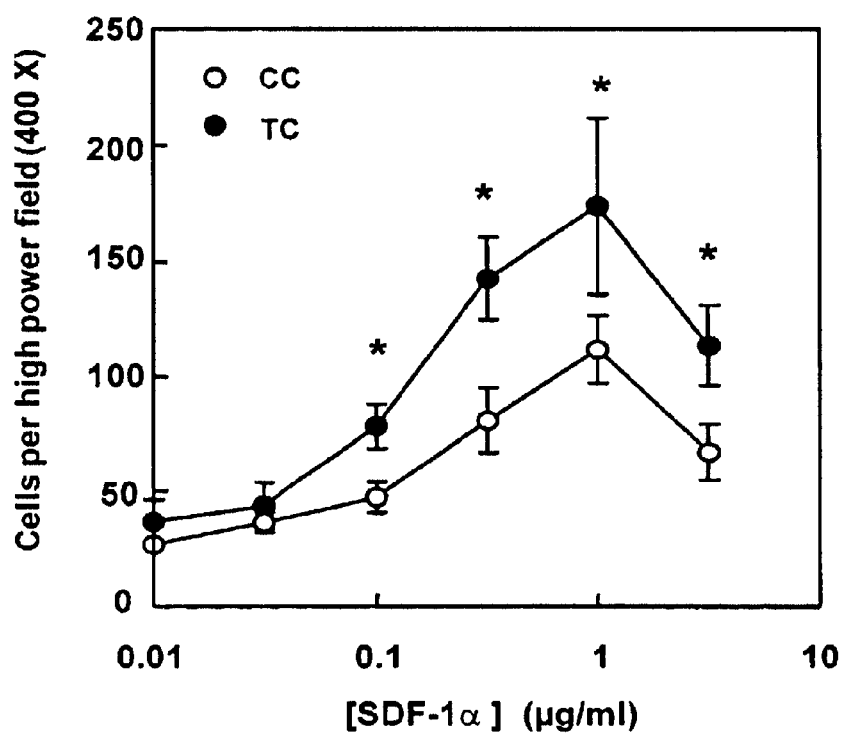
FIG. 7 illustrates an increased chemotactic response of the cells of 825T allele carriers compared to cells of homozygotic C825 allele carries after stimulation with the stromal cell-derived factor 1 alpha (SDF 1 alpha).

T lymphocytes play an important role in the human immune system and mediate the cellular immune response there. Increased activation capacity of T lymphocytes results among others, as already mentioned, in transplanted organs (kidney, liver, heart, lungs, pancreas among others) being subject to an intensified immunological attack. FIG. 7 shows as one example the chemotaxis of human T lymphocytes after stimulation with the stromal cell-derived factor 1alpha (SDF 1alpha). A clearly increased chemotactic response of the cells of 825T allele carriers compared to cells of homozygotic C825 allele carriers is apparent.

Similarly, T lymphocytes of 825T allele carriers respond intensely after stimulation with other chemokines, for example RANTES. This behavior is due to the fact that the chemotactic response is controlled essentially by betagamma subunits of heterotrimeric G proteins (Arai, H., Tsou, C. L. and Charo, I. F. Chemotaxis in a lymphocyte cell line transfected with C-C chemokine receptor 2B: Evidence that directed migration is mediated by betagamma dimers released by activation of Galphai-coupled receptors. (Proc.Natl.Acad.Sci.U.S.A. 94(26): 14495–14499, 1997).

The intensified activation of T lymphocytes of 825T allele carriers is also expressed in the increased proliferation of these cells compared to T lymphocytes of homozygotic C825 allele carriers.

Thus, it can be predicted overall that the T lymphocytes of 825T carriers react more strongly to suitable stimulation; this is expressed in increased proliferation and chemotaxis.

This behavior is manifested in the form of increased cellular immune defense; this is especially relevant in conditions and surgeries in which there is increased cellular immune defense. Immunological attacks on transplanted organs (kidneys, liver, pancreas, bone marrow, heart, etc.) should be mentioned here in particular. It can thus be predicted that 825T allele carriers tend increasingly to develop acute or chronic rejection reactions against these transplanted organs. This rejection reaction is further strengthened if the transplanted organs originate from a donor who himself is a carrier of the 825T allele. This is due to the fact that organs and tissues of these donors react more strongly to increased immunological attacks by the cells of the recipients in the presence of a 825T allele. Furthermore there is an intensified reaction in acute or chronic virus infections.

7. Prediction of an Intensified Progression of AIDS

The multiplication of the HIV virus in T lymphocytes is increased by the activation of the chemokine receptors with action which is mediated via activation of G proteins (Kinter, A., Catanzaro, A., Monaco, J., Ruiz, M., Justement, J., Moir, S., Arthos, J., Oliva, A., Ehler, L., Mizell, S., Jackson, R., Ostrowski, M., Hoxie, J., Offord, R., and Fauci, A. S. CC chemokines enhance the replication of T-tropic strains of HIV-1 in CD4(+) T cells; role of signal transduction. Proc.Natl.Acad. Sci. U.S.A. 95(20): 11880–11885, 1998).

Thus it can be expected that in the T lymphocytes of 825T allele carriers who have increased activation capacity of the G proteins increased virus multiplication takes place after HIV infection. Thus these patients have increased risk of developing AIDS earlier after HIV infection than HIV-positive patients who are homozygotic for the C825 allele on the GNB3 locus. In the following table the genotype distribution of 515 HIV-positive patients and of 622 HIV-negative blood donors is shown.

TABLE VIII

|   | HIV positive | HIV negative |
|---|---|---|
| TT | 64 | 56 |
| TC | 235 | 276 |
| CC | 216 | 290 |
| Total | 515 | 622 |
| T-allele frequency | 35.2% | 31.2% |

There is a significant difference of the genotype distribution between healthy control probands and HIV-positive individuals (chi square=4.253, 1 degree of freedom, p=0.0392; chi square test for trend). The risk for the TT versus the CC genotype to be HIV positive is thus 1.5 (1.0–2.3; p=0.035; chi square=4.4).

There is a further accumulation of the 825T allele within the group of HIV positive patients who have developed AIDS and their number of CD4-positive cells has dropped to less than 200 per milliliter of blood, as shown below:

TABLE IX

|   | HIV positive, CD4 <200 cells/µl blood | HIV positive, CD4 ≧200 cells/µl Blood |
|---|---|---|
| TT | 40 | 14 |
| TC | 122 | 89 |
| CC | 113 | 80 |
| Total | 275 | 183 |
| T-allele frequency | 36.7% | 32% |

Thus, in HIV-positive patients who carry the 825T allele there is an increased risk of developing AIDS. For homozygotic 825 allele carriers the risk is doubled compared to the homozygotic C825 allele carriers (OR TT/CC=2.0 (1.0–3.9; p<0.05)).

Genotyping on the GNB3 locus therefore offers the possibility that an increased risk is assigned to the HIV-positive 825T allele carriers for exhibiting an intensified progression of the disease, especially increased multiplication of the AIDS virus occurring. Furthermore, the risk of a more rapid drop of CD4 cells is associated with it.

Within the framework of infection with the HIV virus (sexual transmission), first of all, generally involvement of macrophages, monocytes and Langerhans cells takes place. So-called "M-tropic" "R5" HIV viruses use among others a chemokine receptor of the CCR5 type to enter these cells. Individuals in whom a homozygotic CCR5_32 deletion can be detected have a reduced risk for HIV infection. Individuals in whom the CCR5_32 allele is present in heterozygotic form show a prolonged interval from HIV infection to seroconversion, or delayed progression of the disease. (1. Quillent, C., Oberlin, E., Braun, J., Rousset, D., Gonzales-Canali, G., Metais, P., Montagnier, L., Virelizer, J. L., Arenzana-Seisdedos, F., and Beretta, A. HIV-1 resistance phenotype conferred by combination of two separate inherited mutations of CCR5 gene. Lancet 351(9095): 14–18, 1998; 2. Mummidi, S., Ahuja, S. S., Gonzales, E., Anderson, S. A., Santiago E. N., Stephan, K. T., Craig, F. E., O'Connell, P., Tryon, V., Clark, R. A., Dolan, M. J., and Ahuja, S. K. Genealogy of the CCR5 locus and chemokine system gene variants associated with altered rates of HIV-1 disease progression. Nat. Med. 4(7): 786–793, 1998; 3. Magierowska, M., Theordoru, I., Debre, P., Sanson, F., Autran, B., Riviere, Y., Charron, D. and Costagliola, D. Combined genotypes of CCR5, CCR2, SDF1, and HLA genes can predict the long-term nonprogressor status in human immunodeficiency virus-1 infected individuals. Blood 93(3): 936–941, 1999; 4. Michael, N. L., Louie, L. G., Rohrbaugh, A. L., Schultz, K. A., Dayhoff, D. E., Wang, C. E., and Sheppard, H. W. The role of CCR5 and CCR2 polymorphisms in HIV-1 transmission and disease progression [see comments]. Nat. Med. 3(10): 1160–1162, 1997; 5. Fauci, A. S. Host factors and the pathogenesis of HIV-induced disease. Nature 384:529–534, 1996.

In contrast, the presence of one variant in the CCR5 promoter (CCR5P1) intensifies AIDS progression, especially in homozygotic CCR5P1 carriers. (Martin, M. P., Dean, M., Smith, M. W., Winkler, C., Gerrard, B., Michael, N. L., Lee, B., Doms, R. W., Margolick, J., Buchbinder, S., Goedert, J. J., O'Brien, T. R., Hilgartner, M. W., Vlahov, D., O'Brien, S. J., and Carrington, M. Genetic acceleration of AIDS progression by a promoter variant of CCR5. Science 282 (5395): 1907–1911, 1998.)

As the disease continues the type of virus changes such that the so-called "T-tropic" (X4) viruses predominate and then attack mainly CD-4-positive T lymphocytes. These viruses enter via the G protein coupled CXCR4-chemokine receptor, the natural ligands of which include among others Stromal Cell Derived Factor 1alpha (SDF-1alpha). A series of chemokines (SDF-1alpha, RANTES, etc.) stimulate the multiplication of T-tropic viruses in CD4-positive T cells, and signal transmission via the pertussis-toxin sensitive G proteins assumes decisive importance: Inhibition of G protein activation by incubation of cells with pertussis toxin reduces the virus replication especially at a low virus number. (Kinter, A., Catanzaro, A., Monaco, J., Ruiz, M., Justment, J., Moir, S., Arthos, J., Oliva, A., Ehler, L., Mizell, S., Jackson, R., Ostrowski, M., Hoxie, J., Offord, R., and Fauci, A. S. CC-chemokines enhance the replication of T-tropic strains of HIV-1 in CD4(+) T cells: role of signal transduction. Proc.Natl.Acad. Sci. U.S.A. 95(20): 11880–11885, 1998).

Conversely, the conclusion can be drawn that in the presence of a 825T allele which indicates the expression of Gβ33-s and Gβ3-s2 and increased activation capacity of G proteins and that the replication of these viruses and thus AIDS progression should be increased.

A change in the gene which codes for SDF-1 (G→A transition at position 801, counted from the start codon) is called SDF1-3'UTR-801G-A or SDF1-3'A. Homozygotes SDF1-3'A show a reduced progression to AIDS. (Winkler, C., Modi, W., Smith, M. W., Nelson, G. W., Wu, X., Carrington, M., Dean, M., Honjo, T., Tashiro, K., Yabe, D., Buchbinder, S., Vittinghoff, E., Goedert, J. J., O'Brien, T. R., Jacobson, L. P., Detels, R., Donfield, S., Willoughby, A., Gomperts, E., Vlahov, D., Phair, J., and O'Brien, S. J. Genetic restriction of AIDS pathogenesis by an SDF-1 chemokine gene variant. ALIVE Study, Hemophilia Growth and Development Study (HGDS), Multicenter AIDS Cohort Study (MACS), Multicenter Hemophilia Cohort Study (MHCS), San Francisco City Cohort (SFCC) [see comments]. Science 279 (5349: 389–393, 1998.)

Figure 9:
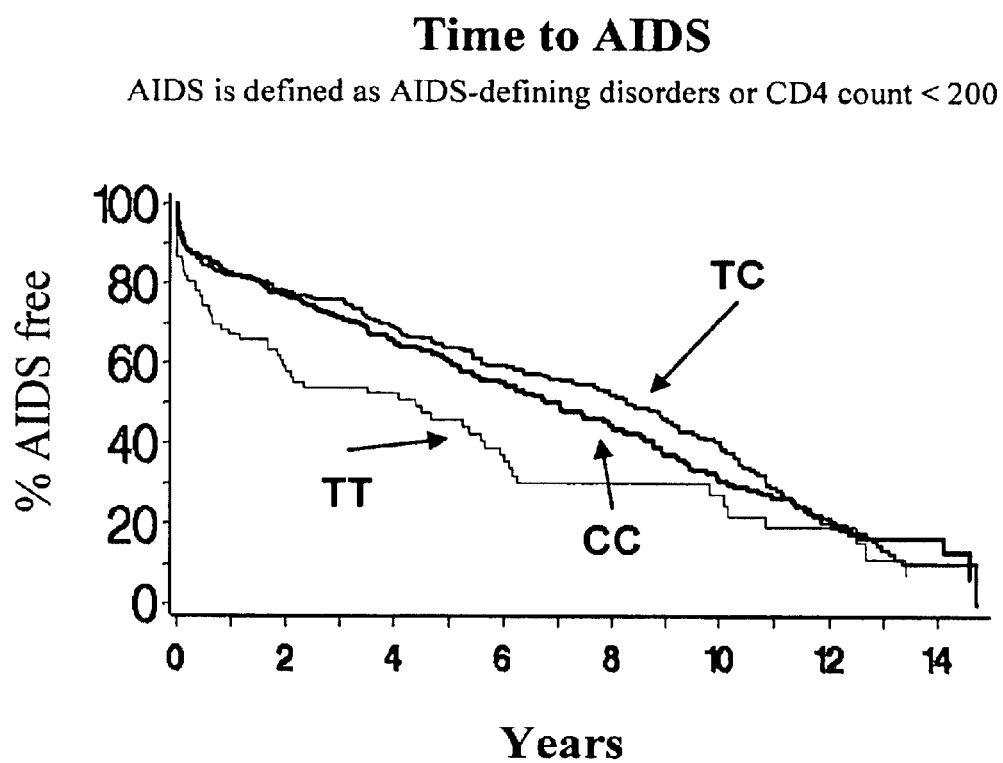
FIG. 9 illustrates that homozygotic 825T allele carriers reach the end point AIDS according to the 1993 CDC definition significantly earlier than homozygotic or heterozygotic 825C allele carriers.

To detect an intensified AIDS progression of 825T allele carriers, 690 HIV-positive homosexuals and heterosexuals (men and women) in whom the HIV virus was transmitted sexually were studied. After genotyping, the following end points of the disease were established which represent one possible definition of developing AIDS:

1. AIDS. Here AIDS is defined as AIDS-defining disease or CD4 cell number<200. This AIDS definition corresponds to the AIDS definition revised in 1993 from the Center for Disease Control (CDC; Atlanta, USA).
2. CD4 cell number<200.
3. Minimum CD4 cell number
4. Maximum virus load FIG. 9 shows the instant from the first positive HIV test to the AIDS diagnosis as Kaplan-Meier curves depending on the genotype. FIG. 9 shows that homozygotic 825T allele carriers reach the end point AIDS according to the 1993 CDC definition significantly earlier than homozygotic or heterozygotic 825C allele carriers.

Figure 10:
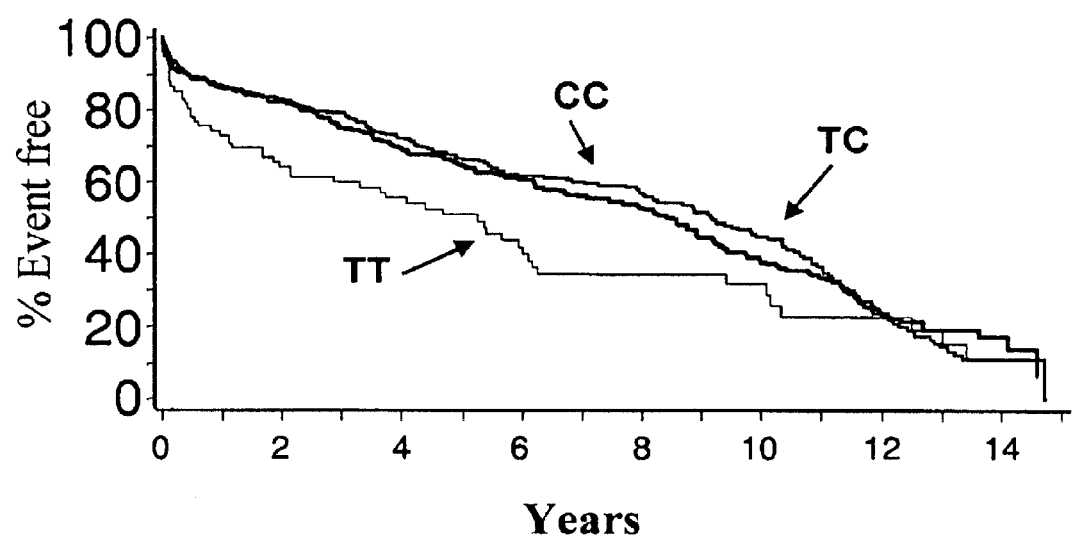
FIG. 10 illustrates the interval between the first positive HIV tests and the drop of the CD4 cell number below 200. Also shown is the drastically accelerated time behavior for homozygotic 825T allele carriers compared to homozygotic and heterozygotic C825 allege carriers.

FIG. 10 shows the interval between the first positive HIV tests and the drop of the CD4 cell number below 200. Here the time behavior for homozygotic 825T allele carriers compared to homozygotic and heterozygotic C825 allele carriers is likewise drastically accelerated.

Figure 11:
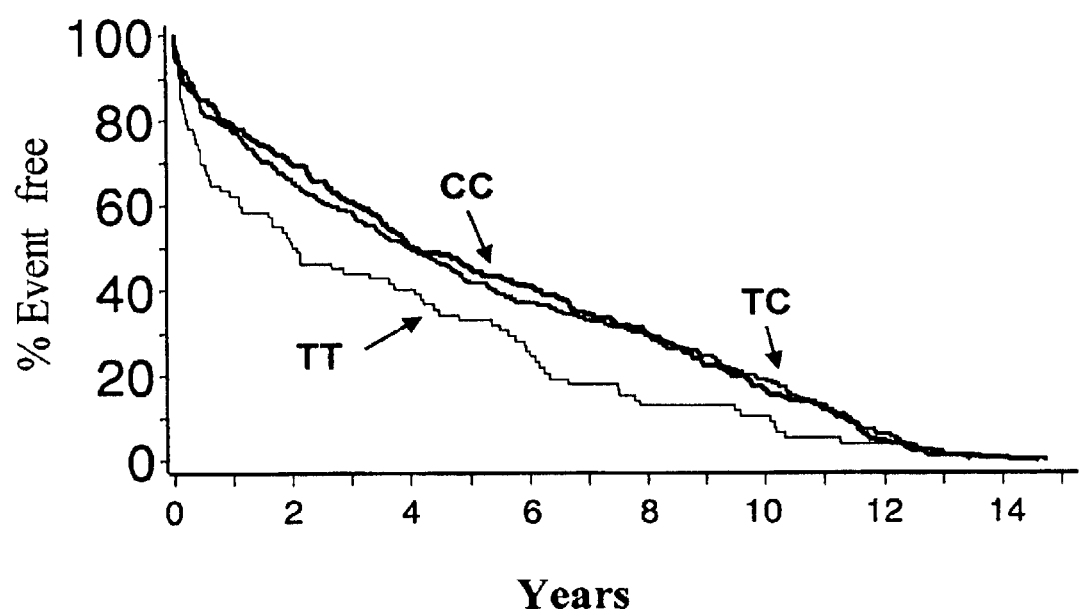
FIG. 11 shows the time behavior from the first positive HIV test and the individually lowest CD4 cell number. Also illustrated is the significant acceleration that arises in homozygotic 825T allele carriers compared to homozygotic and heterozygotic C825 allele carriers.

FIG. 11 shows the time behavior from the first positive HIV test and the individually lowest CD4 cell number. Here likewise a significant acceleration arises in homozygotic 825T allele carriers compared to homozygotic and heterozygotic C825 allele carriers.

Figure 12:
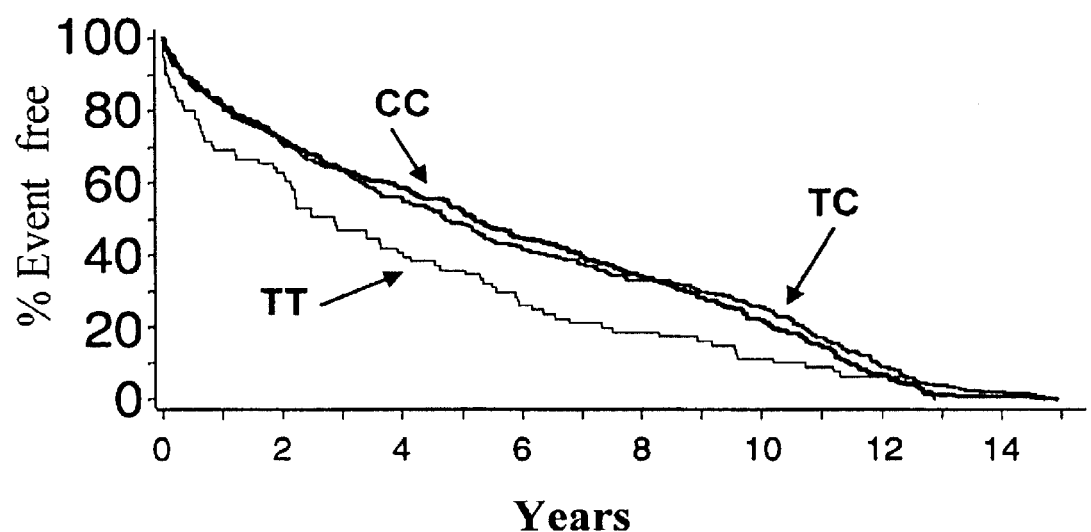
FIG. 12 shows the interval between the first positive HIV test and the maximum virus load. Also illustrated is the increased risk of 825T allele carriers of having a maximum virus load earlier than homozygotic or heterozygotic C825 allele carriers.

FIG. 12 shows the interval between the first positive HIV test and the maximum virus load. In turn it is shown that the 825T allele carriers have a clearly increased risk of having a maximum virus load earlier than homozygotic or heterozygotic C825 allele carriers.

7.1 Correlation to the CCR5 Allele Status

In the following, the CCR5 allele status was also studied with reference to the presence of the _32 deletion. The relative risks (RH) shown in the following table are shown together with the 95% confidence intervals (95% CI).

Without considering the genetic background, the risk for AIDS or the drop of the CD4 cell level<200 is roughly doubled for homozygotic 825T allele carriers compared to homozygotic and heterozygotic C825 allele carriers. Ignoring the genetic background the risk for CCR5_32 allele carriers to reach a CD4 cell number<200 is increased by a factor of 1.4 in the observation intervals. In the following the effect of the 825T allele is studied separately for the CCR5 wild type and for CCR5_32 wild type. In the presence of the homozygotic CCR5 wild type the risk for AIDS or a CD4 cell number<200 is roughly 1.6 for homozygotic 825T allele carriers compared to heterozygotic C825 allele carriers.

In the presence of the CCR5_32 genotype which was described originally as protective, for homozygotic 825T allele carriers, there is a further increase of the risk by almost 3-fold compared to heterozygotic C825 allele carriers, as depicted below:

TABLE X

GNB3 825 Genotype status and CCR5-Genotype status and AIDS-Progression COX Proportional Hazard Model:

| Constant | Target quantity | Gene status studied | RH | 95% CI |
| --- | --- | --- | --- | --- |
| Nothing | AIDS | GNB3 TT versus TC + CC | 1.9 | (1.4–2.6) |
|  | CD4 <200 | " | 1.9 | (1.4–2.6) |
|  | CD4 min | " | 1.5 | (1.2–2.0) |
|  | PCR max | " | 1.5 | (1.2–2.0) |
| Nothing | AIDS | CCR5 WT versus CCR5Δ32 | ns | |
|  | CD4 <200 | " | 1.4 | (1.0–1.9) |
|  | CD4 min | " | ns | |
|  | PCR max | " | ns | |
| CCR 5 = WT | AIDS | GNB3 TT versus TC + CC | 1.6 | (1.1–2.3) |
|  | CD4 <200 | " | 1.6 | (1.1–2.3) |
|  | CD4 min | " | 1.4 | (1.1–1.9) |
|  | PCR max | " | 1.4 | (1.0–1.9) |
| CCR5 Δ32 | AIDS | GNB3 TT versus TC + CC | 2.7 | (1.3–5.5) |
|  | CD4 <200 | " | 3.0 | (1.5–6.3) |
|  | CD4 min | " | 2.1 | (1.1–3.8) |
|  | PCR max | " | 1.9 | (1.0–3.4) |

RH = relative hazard; 95% CI = 95% confidence interval; GNB3 = G protein beta3 subunit; TT - Homozygote for 825T; TC and CC, heterozygotic or homozygotic for C825; CCR5 WT - CCR5 wild type (absence of Δ32 deletion); PCR-max, time interval to maximum virus load; AIDS, time interval to advent of AIDS according to 1993 CDC definition; ns - not significant Therefore, in summary the following can be stated for HIV-positive patients:
1. Homozygosis for the 825T allel in GNB3 increases the risk for the progression AIDS; and
2. This effect is further intensified in the presence of the CCR5Δ32 genotypes.

8. Prediction of Osteoporosis

Generalized osteoporosis represents one of the most frequent diseases of post menopausal women and entails an increased risk of bone fractures. G proteins are significantly involved in processes which lead to rebuilding bone. The altered activation capacity of G proteins is thus heavily involved in the osteoporosis risk (May, L. G. and Gay, C. V. Multiple G protein involvement in parathyroid hormone regulation of acid production by osteoclasts. J. Cell Biochem 64(i): 161–170, 1997; Gordeladze, J. O., Lund, H. W., Jablonski, G., and Bruland, O. S. Diverse expression of G proteins in human sarcoma cell lines with different osteogenic potential: Evidence for the involvement of $G_{12}$ in cell proliferation. J. Cell Biochem. 60:95–106, 1996).

In this case as well female carriers of the GNB3-825T allele show an increased risk of developing osteoporosis.

9. Prediction of Alzheimer's Disease

Altered activation capacity of G proteins and altered regulation of $K^+$ channels have been described in patients with Alzheimer's disease. Furthermore, reduced activation of the adenylcyclase after stimulation of beta-adrenergic receptors was described. These phenomena can be attributed to increased activation capacity of pertussis toxin-sensitive G proteins with expression of the Gβ3s splice variant (Okamoto, T., Takeda, S., Murayama, Y., Ogata, E. and Nishimoto, I. Ligand-dependent G protein coupling function of amyloid transmembrane precursor. J.Biol. Chem. 270: 4205–4208, 1996; Nishimoto, I., Okamoto, T., Matsuura, Y., Takahasi, S., Murayama, Y., and Ogata, E. Alzheimer amyloid protein precursor complexes with brain GTP-binding protein $G_o$. Nature 362:75–79, 1993; Etcheberrigaray, R., Ito, E., Oka, K., Tofel-Grehl, B., Gibson, G. E. and Alkon, D. L. Potassium channel dysfunction in fibroblasts identifies patients with Alzheimer disease. Proc.Natl.Acad.Sci. USA. 90: 8209–8213, 1993; Yamatsuji, T., Matsui, T., Okamoto, T., Komatsuzaki, K., Zakeda, S., Fukumoto, H., Iwatsubo, T., Suzuki, N., Asami-Odaka, A., Ireland, S., Kinane, T. B., Giambarella, U., and Nishimoto, I. G protein-mediated neuronal DNA fragmentation induced by familial Alzheimer's disease-associated mutants of APP. Science 272:1349–1352, 1996; Cowburn, R. F. Wiehager, B., Ravid, R., and Winblad, B. Acetylcholine muscarinic M2 receptor stimulated [$^{35}$S]GTPgammaS binding shows regional selective changes in Alzheimer's disease postmortem brain. Neurodegeneration 5:19–26, 1996).

Consequently, carriers of the GNB3-825T allele have an increased risk of developing Alzheimer's disease. At the same time the early-onset atherosclerosis described under 3 which is observed in carriers of the GNB3-825T allele contributes to the formation of Alzheimer's disease.

10. Prediction of Erectile Dysfunction (Impotence)

The erection of the penis after sexual stimulation is caused by increased inflow of blood with simultaneously reduced outflow of blood. The mechanisms which are necessary for the increased inflow of blood comprise the actions of hormones, the action of which is mediated via G proteins.

A total of 63 males with proven erectile dysfunction and 614 healthy male controls were genotyped on the GNB locus 825 locus, the results are shown below:

TABLE XI

|  | Erectile Dysfunction | Control Males |
| --- | --- | --- |
| TT | 2 (3) | 55 (9) |
| TC | 20 (32) | 275 (45) |
| CC | 41 (65) | 284 (46) |
| Total | 63 | 614 |
| FT (%) | 19.0% | 31.4% |

The figures are n %.

The distribution of genotypes is significantly different (chi-square=8.7; 2 degrees of freedom, p=0.01), in the males with erectile dysfunction a drastic reduction of the frequency of the 825T allele to 19% being conspicuous. In this way the following risks (odds ratios; OR) can be computed for erectile dysfunction in comparison to a randomized control group:

CC/TT, OR=4.0 (95% Cl: 0.9–16.9; p=0.04)
CC/TT, OR=2.0 (95% Cl: 1.1–3.5; p=0.01)

Thus homozygotic C825 allele carriers compared to homozygotic 825T allele carriers have 4 times the risk, compared to heterozygotic 825T allele carriers twice the risk of developing an erectile dysfunction. Furthermore, the risk for heterozygotic 825T allele carriers is roughly doubled compared to homozygotic 825T allele carriers.

11. Prediction of Thyroid Gland Dysfunctions

Carriers of the 825T allele often have thyroid gland dysfunctions and must be treated with thyroid hormones (for example thyroxin).

12. Prediction of Increased Pregnancy Risk

Hypertension, edema formation and the so-called "HELLP syndrome" entail a serious danger for pregnancy, both for the life of the mother and also the life of the fetus. It was found that in carriers of the 825T allele who develop gestational hypertension (gestosis, preeclampsia) there is a high risk of premature birth (delivery before the 37th week of pregnancy or birth weight of the child less than 2500 g, see also 14.), for these children in addition there being the risk for stillbirth or post-delivery death. At the same time in women who are carriers of the 825T allele and who are suffering from gestosis, the risk of spontaneous abortion (habitual abortion) increases.

Detection of the 825T allele is therefore suited for predicting an increased risk of death for the unborn child of pregnant mothers with gestosis.

Gestosis (preeclampsia) is a serious condition which is accompanied by high blood pressure, edema, and proteinuria. The gestosis is associated with an increased risk for the pregnant mother, but especially for the unborn child. A total of 188 women without gestosis and 191 women with gestosis were studied. Here the gene status at the GNB3 locus and the gene status with respect to Glu298Asp variant in the gene which codes for endothelial NO synthase (eNOS) were studied (Yoshimura et al. "A missense Glu298Asp variant in the endothelial nitric oxide synthase gene is associated with coronary spasm in the Japanese, Hum Genet. 1998 Jul; 103(1): 65–9).

With the simultaneous presence of a 825T allele in GNB3 (TC or TT genotype) the homozygotic presence of the 298Asp variant in eNOS leads to a gestosis risk ten times higher. With the simultaneous presence of a 825T allele in the GNB3 (TC or TT genotype) the heterozygotic presence of the 298Asp variant in eNOS leads to twice the gestosis risk.

13. Prediction of Low Birth Weight

There is recognized to be an empirical relationship which describes an inverse relation between birth weight and the risk of suffering from obesity, hypertension or type-2 diabetes over the lifespan. Here it has been described that individuals with very low birth weight tend especially to these conditions. It was therefore studied whether for children with the 825T allele there is an increased risk of being born with a low birth weight. A low birth weight has been defined as the weight which after dividing all weights is in the lowest quartile of the overall distribution. If we compare the distribution of genotypes on the GNB3 locus between the 1st quartile with the combined quartiles 2–4, for homozygotic 825T allele carriers compared to homozygotic C825 allele carriers the risk of low birth weight is increased by a factor of six (95% CI=1.3–28.6; p<0.05) (quartile 1 versus quartiles 2–4) and for heterozygotic 825T allele carriers the risk is 2.4 times higher (95% CI=0.7–7.9)

TABLE XII

| G beta3 gene 825T allele and birth weight | | | | | |
| --- | --- | --- | --- | --- | --- |
|  | 1. Quartile | 2. Quartile | 3. Quartile | 4. Quartile | 2.–4.Quar-tile |
| Birth weight | –3130 g | –3430 g | –3750 g | >3750 g | All > 3130 g |
| TT | 5 | 1 | 2 | 2 | 5 |
| TC | 11 | 9 | 11 | 7 | 27 |
| CC | 5 | 11 | 8 | 11 | 30 |
| Total | 21 | 21 | 21 | 20 | 62 |
| % T | 50 | 26 | 36 | 27.5 | 30 |

After genotyping on the GNB3 locus therefore an increased risk is assigned to 825T allele carriers for being born with low birth weight and being subjected to intrauterine growth retardation.

14. Pharmacogenetics

Another subject of this invention is the pharmacogenetics of the GNB3-825T allele, i.e. the possibility of predicting the action of pharmaceuticals using the genotype.

Most pharmaceuticals (hormones, receptor agonists) exert their effect via receptors which couple to G proteins. Antagonists block the hormone receptor interaction.

It has now been ascertained that genotyping on the GNB 3 locus is suitable for predicting the effectiveness of pharmaceuticals using the genotype. This relates to responsivity in vivo to hormones, transmitters (also neurotransmitters) or pharmaceuticals which activate those G protein heterotrimers which contain the G protein subunits Gβ3 and Gβ3s. This goes along with the prediction of reduced effectiveness of hormones, neurotransmitters or pharmaceuticals which stimulate the G-protein subunit, for example beta adrenergic agonists. This also applies with the simultaneous use of detection of the Arg16Gly variant and the Gln27Glu variant in the β2 adrenergic receptor. The presence of the GNB3-825T allele therefore shows altered pharmacogenetics and should be considered in the specific choice of a form of therapy (pharmacological or non-pharmacological) and in the dosages of pharmaceuticals or hormones in hypertension, diabetes mellitus, coronary heart disease, acute myocardial infarction with or without cardiac irregularities, cardiac irregularities, transplant rejection, erectile dysfunction, etc.

14.1 Erythropoietin

In this connection the presence of the GNB3-825T allele however also allows the prediction of the effectiveness of administering erythropoietin on blood cell formation and the prediction of the occurrence of hypertension during this therapy as well as the prediction of the danger of developing hypertension during immunosuppressive therapy (for example, with cyclosporin).

14.2 Agonists on the Serotonin Receptor

Likewise in this connection the effectiveness of substances for treatment and prevention of migraine attacks (agonists on the serotonin receptor) can be predicted.

Figure 8:
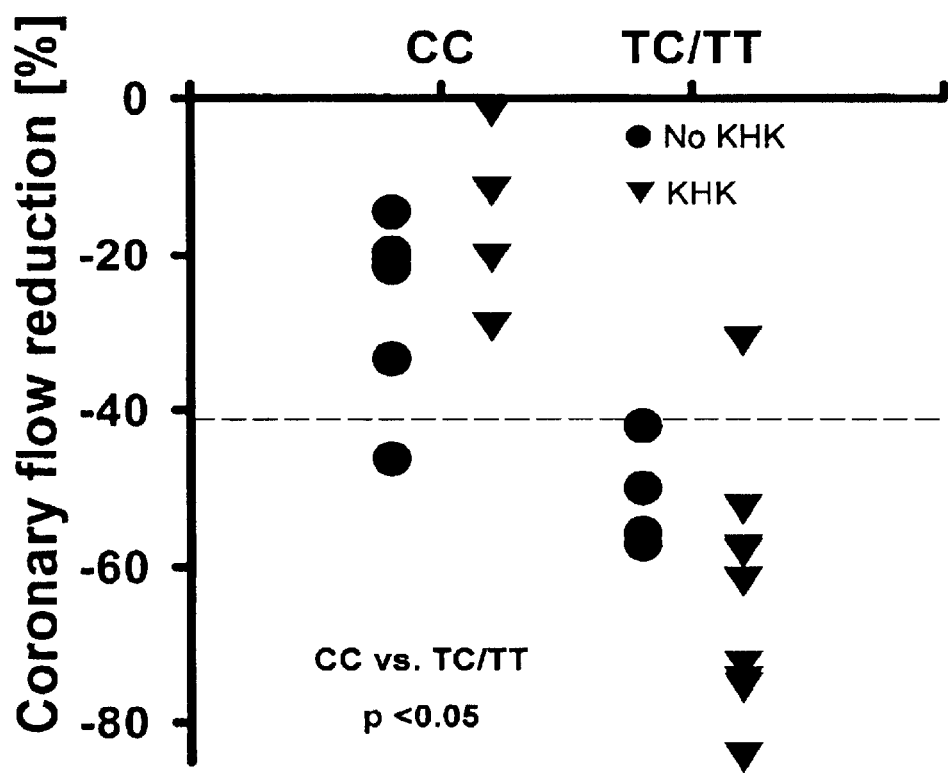
FIG. 8 illustrates an intensified reduction of coronary blood flow in carriers of the GNB3-825T allele

This is demonstrated on the following example. An alpha2 adrenergic agonist (BHT 933) was applied intracoronary in the probands; it leads to contraction of coronary vessels. This effect was quantified via the flow change through these sections of the vessels. As FIG. 8 shows, an intensified reduction of coronary blood flow in carriers of the GNB3-825T allele is observed, regardless of whether they are suffering from a coronary heart disease (CHD). This means that in carriers of the GNB3-825T allele the intensification of the action of these pharmaceuticals can be predicted.

14.3 Beta-adrenoceptor Blockers

Another example of the use of genotyping on the GNB3 locus is the prediction of the effectiveness of substances which block beta-adrenergic receptors. Here it can be stated that young healthy 825T allele carriers (homozygotic and heterozygotic) compared to homozygotic C825 allele carriers have an increased cardiac output (TC/CC=92.9±4.1 ml (n=30); CC=74.7±4.0 ml (n=19); p<0.01). After intravenous administration of the beta-adrenoceptor blocker propanolol the cardiac output decreases on the average by 3 ml in homozygotic C825 carriers, conversely by 12 ml in homozygotic and heterozygotic 828T allele carriers (p<0.05). In the same way there is an intensified reduction of the cardiac output in 825T allele carriers. Thus, by establishing the GNB3 C825T status the pharmacological-physiological action of blockage of beta-adrenergic receptors can be predicted. This relates not only to non-selective beta blockers such as the indicated propanolol, but to all beta adrenoceptor blockers, therefore also selective β1 and β2 receptor blockers.

14.4 Prostaglandin E1

When erectile dysfunction is present, prostaglandin E1 is injected into the corpus cavemosum for diagnostic clarification, but also possibly to begin long-term therapy. Prostaglandin E1 activates adenylcyclase, and the subsequent formation of cAMP relaxes smooth vascular muscle cells and thus induces an increased arterial blood flow and thus erection of the penis. The degree of the erection which occurs can be quantified via a point system (score 0–5). Here the scores 4 and 5 correspond to an erection which is sufficient for penetration, while scores<4 can be considered as insufficient.

In 87 males with penile dysfunction, 10 micrograms of prostaglandin E1 were administered with quantification of the erection score. Here the genotype distribution was as follows: Sufficient erection (scores 4 and 5): TT=3; TC=15; CC=16; (frequency of GNB3 825T allele: 30.9%). Insufficient or absent erection: TT=3; TC=16; CC=34; (frequency of the GNB3 825T allele: 20.8%). Similarly, in homozygotic C825 allele carriers after injection of prostaglandin E1 there is a reduced increase of the arterial blood flow which was measured using doppler sonography.

Thus roughly twice the risk of not reacting to the injection with prostaglandin E1 with a sufficient erection is assigned to homozygotic 825T allele carriers.

15. Gβ3 Inhibitors

Another subject of this invention is production of pharmaceuticals which inhibit the Gβ3s splice variant.

Fundamentally it is possible to synthesize chemicals which inhibit the function of the Gβ3s protein by their leading for example to accelerated decomposition of the protein or by inhibiting its interaction and combination with alpha and gamma subunits of the human G protein. To identify these substances a screening system is necessary. To do this the expression of the Gβ3s subunit alone or in combination with different Galpha and Gβ subunits in Sf9 insect cells, in other cells suitable for transfection, or the use of purified Galpha and Ggammaβ3s subunits in a reconstitution system in the presence or absence of G-protein-coupled receptor is suitable. By means of these systems for example the action of chemicals on the receptor-mediated binding of GTP to the Galpha subunits can be studied, by which ultimately chemicals can be identified which inhibit the function of the Gβ3s subunit. One such test system can fundamentally also be used as a "high-throughput screening system" for testing of a host of substances.

Second Splice Variant of the Gbeta3s-3 Protein (Gbeta3s-2)

Another splice variant of the Gbeta3s subunit of heterotrimeric G proteins of man which is called Gβ3s-2 was found by further analyses of the GNB3 gene.

To do this, the mRNA was extracted using standard methods from neutrophilic granulocytes of individuals who are homozygotic for the C825 in GNB3 (CC genotype) or who are heterozygotic for the C825T polymorphism (TC genotype) and are transcribe by means of the reverse transcriptase reaction in cDNA. The cDNA which codes for Gβ3 was amplified by means of a polymerase chain reaction. Here the following primers were used:

Sense: 5'-gcc gtc aga ctt tca ctg gc-3' (SEQ ID NO: 7)
Antisense: 5'-tgt tca ctg cct tcc act tcc-3' (SEQ ID NO: 8)

The location of these primers is chosen such that there is a primer in the area of exon 9 of the gene, while the other primer is in exon 11 in the 3' untranslated area.

The following PCR conditions were used: 5 min: 94° C.—1 min., 60° C.—45 sec., 72° C.—1 min.; finally: 72° C.—7 min.

PCR products were separated in a 2.5% agarose gel in 0.5× TBE plus 0.1 microns/ml ethidium bromide and visualized under UV light. pBR322 DNA/Alu I was used as the size marker.

Figure 13:
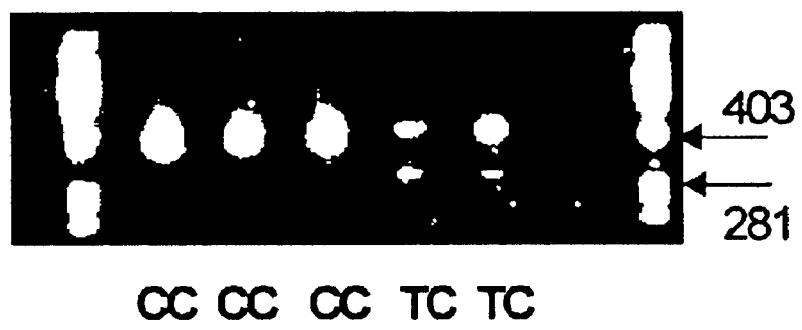
FIG. 13 illustrates the detection of a specific shortened RT-PCR product in cells of individuals who carry a T allele on position 825 of the cDNA (heterozygotic or homozygotic).

As becomes apparent in FIG. 13, in cells of individuals who carry a T allele on position 825 of the cDNA (heterozygotic or homozygotic) another specific shortened RT-PCR product is detected.

It has been found that the shortened PCR product represents a new splice variant of the Gβ3 gene. A representation of it can be found in Appendix 3. The complete sequence of the cDNA is shown, as was described earlier by Levine et al. (Levine, M. A., Smallwood, P. M., Moen, P. T. Jr., Helman, L. J. and Ahn, T. G. Molecular cloning of β3 subunit, a third form of the G protein beta-subunit polypeptide. Proc.Natl.Acad.Sci. U.S.A. 87(6), 2329–2333 (1990)). Here the numbering originally stipulated by the authors is retained so that the start codon ATG is assigned to position 6 of the nucleic sequence.

The previously described deletion of nucleotides 504–626 (corresponding to 498–620 if numbering begins with the start codon ATG) which is caused by alternative splicing of the gene in carriers of a 825T allele is described. In Appendix 3 this area is called "deletion in Gβ3s" (Siffert, W., Rosskopf, D., Siffert, G., Horsthemke, B. Association of the human G protein β3 subunit variant with hypertension Nat. Genet. 18(1):45–48, 1998). The deletion which has now been described again occurs in exon 10 of the gene, includes the previously described C825T polymorphism, and comprises 129 nucleotides; this corresponds on the protein plane to a loss of 43 amino acids (in Appendix 3 called "deletion in Gβ3s-2). The open read frame is preserved. The exact location of the deletion cannot be unambiguously ascertained due to repetitive sequences. The nucleotides 708–836 or the nucleotides 712–840 can be omitted. If the ATG of the start codon is fixed with 1, the nucleotides 702–830 or 706–834 are omitted. Knowledge of the exact location of this deletion is insignificant for the new cDNA and amino acid sequences of Gβ3s-2. Appendix 3 furthermore shows the polymorphism positions C825T and C1423T. Due to the use of the original numbering according to Levine et al. in Appendix 3 the C825T polymorphism is at position 831 and C1243T polymorphism at position 1249. A new T657A polymorphism which occurs in roughly 1–3% of Caucasians was found by further sequencing.

The new cDNA sequence of the Gβ3s-2 is shown combined in Appendix 4 jointly with the amino acid sequence.

Figure 14:
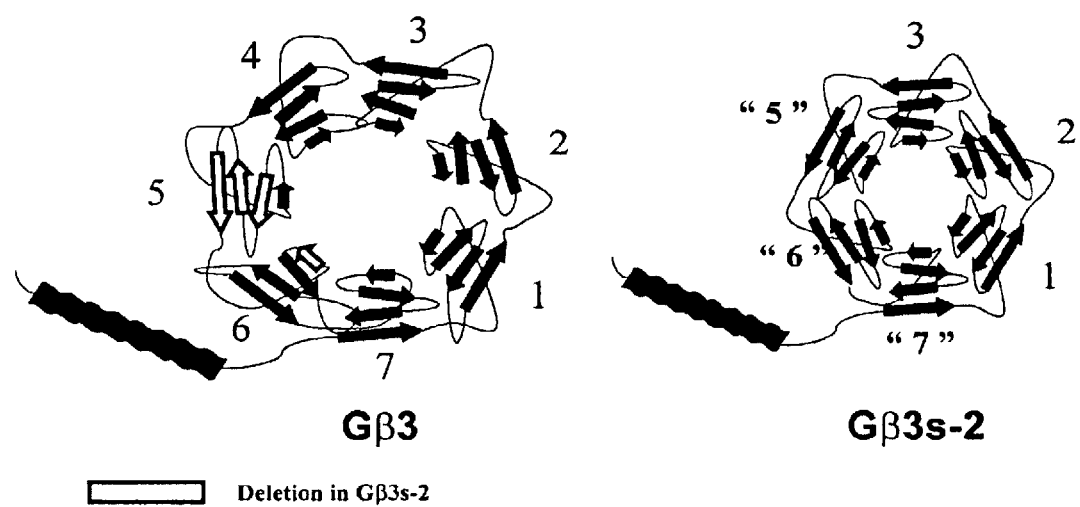
FIG. 14 illustrates the potential structures of Gβ3 and Gβ3s/Gβ3s-2

G protein beta subunits belong to the family of the WD repeat proteins. These beta subunits are highly conserved. It is known that these beta subunits form a spatial structure which is similar to a propeller with seven propeller blades (Sondek, J., Bohm, A., Lambright, D. C., Hamm, H. E. and Sigler, P. B. Crystal structure of a G protein betagamma dimer at 2.1A resolution. Nature 379:369–374, 1996). Based on the deletion which occurs in Gβ3s-2 it can be predicted that a new beta subunit is formed which, analogously to Gβ3-s, has only six instead of seven such rotor blades. This is shown schematically in FIG. 14, at the same time the deletion found previously in Gβ3-s being shown.

Figure 15:
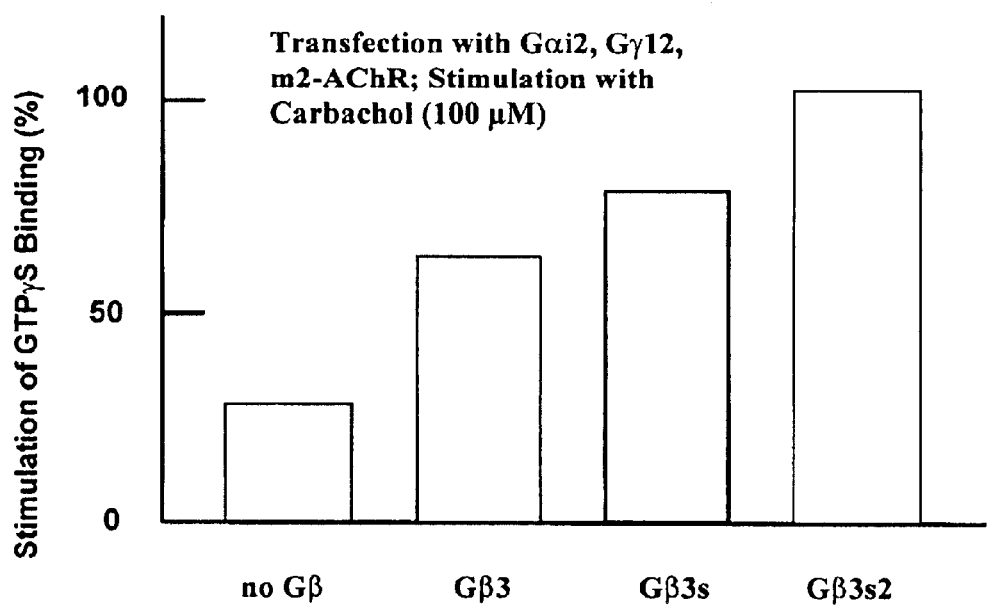
FIG. 15 illustrates that (1) in the absence of a beta subunit only little G protein activation is observed (2) after transfection of Gβ3 or Gβ3s, G protein activation is intensified; and (3) the new splice variant Gβ3s-2 leads to the strongest potentiation of G protein activation cause by the agonist carbachol.

First of all, it was studied whether G protein heterotrimers which contain Gβ3s-2 are functionally active. As described earlier, the Sf9 insect cell system was used for this purpose (Siffert, W., Rosskopf, D., Siffert, G., Busch, S., Moritz, A., Erbel, R., Sharma, A. M., Ritz, E.; Wichmann, H. E., Jakobs, K. H., and Horsthemke, B. Association of a human G protein β3 subunit variant with hypertension. Nat. Genet. 18(1): 45–48, 1998). The cells were transfected with Galphai2, Ggamma12 and the m2-muscarinergic acetylcholine receptor. The bonding of 35S-GTPgammaS to permeabilized cells was quantified after stimulation with carbachol (100 microM). Here the specific incorporation of 35S-GTPgammaS is a measure of the activation of G protein alpha subunits. As shown in FIG. 15, in the absence of a beta subunit only little G protein activation is observed. After transfection of Gβ3 or Gβ3s, G protein activation is clearly intensified, Gβ3s being more potent than Gβ3. The new splice variant Gβ3s-2 leads to the strongest potentiation of G protein activation caused by the agonist carbachol. Thus it is shown at the same time that Gβ3s-2 in spite of the deletion of one propeller blade is functionally active and even leads to intensified activation of G proteins. Thus, earlier findings are also explained which have demonstrated the intensified activation capacity of G proteins in cells of individuals carrying the 825T allele (Siffert, W., Rosskopf, D., Siffert, G., Busch, S., Moritz, A., Erbel, R., Sharma, A. M., Ritz, E.; Wichmann, H. E., Jakobs, K. H., and Horsthemke, B. Association of a human G protein beta3 subunit variant with hypertension. Nat. Genet. 18(1): 45–48, 1998. Pietruck, F., Moritz, A., Montemurro, M., Sell, A., Busch, S., Rosskopf, D., Virchow, S., Esche, H., Brockmeyer, N., Jakobs, K. H., and Siffert, W. Selectively enhanced cellular signalling by $G_i$ proteins in essential hypertension. Galpha$_{i2}$, Galpha$_{i3}$, G-$_1$, and G-$_2$ are not mutated. Circ. Res. 79:974–983, 1996. Siffert, W., Rosskopf, D., Moritz, A., Wieland, T., Kaldenberg-Stasch, S., Kettler, N., Hartung, K., Bechmann, S., and Jakobs, K. H. Enhanced G protein activation in immortalized lymphoblasts from patients with essential hypertension. J. Clin. Invest. 96:759–766, 1995. Wirchow, S., Ansorge, N., Ruebben, H., Wiffert, G., and Siffert, W. Enhanced fMLP-stimulated chemotaxis in human neutrophils from individuals carrying out the G protein beta3 subunit 825T-allele. FEBS Lett. 436(2): 155–158, 1998).

Figure 16:
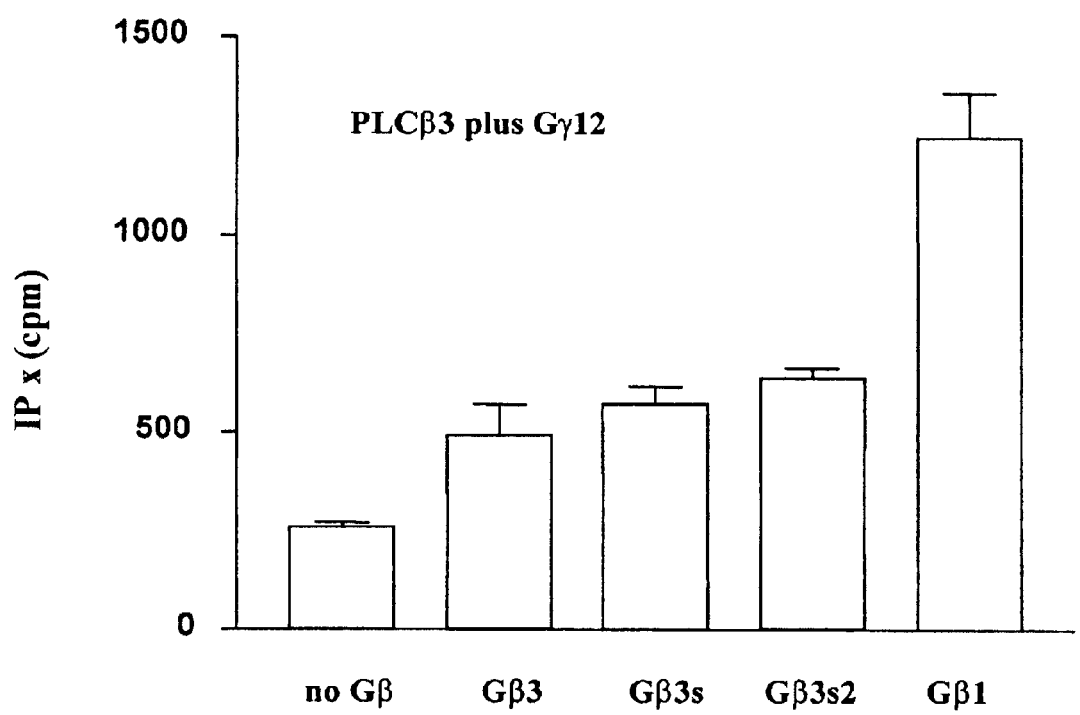
FIG. 16 illustrates that betagamma dimers which contain Gβ3, Gβ3s, or Gβ3s-2 can activate PLCβ3. Activation of PLCβ3 after transfection of Gβ1 is shown for comparison.

It is generally known that betagamma subunits of heterotrimeric G proteins can stimulate different isoforms of the phospholipase Cbeta. This enzyme splits phospholipids, for example phosphatdylinositol-4,5-bisphosphate into the "second messenger" molecules inositol-1,4,5 triphosphate (IP3) and 1,2-diacylglycerol (DAG), IP3 causes release of calcium ions from intracellular reservoirs, while DAG activates different isoforms of the protein kinase C. Activation of phospholipase C is thus an important step in cell activation. It was examined whether betagamma subunits which contain Gβ3s-2 can activate the phospholipase Cβ3 (PLCbeta3). To do this the COS-7 cell system was used which is often used in the generally accessible literature for transient transfection of proteins. These cells were transfected with the PLCβ3, Ggamma12 and different Gβ subunits. The cells were pretreated with radioactively tagged [3H] inositol. The formation of inositol phosphates (IP) was quantified using standard methods, the amount of the 1P formed constituting a measure of the activation of the PLC. As is shown in FIG. 16, betagamma dimers which contain Gβ3, Gβ3s, or Gβ3s-2 can activate PLCβ33. Likewise, activation of PLCβ3 after transfection of Gβ1 is shown for comparison.

These studies prove that Gβ3s-2 is able to cause stimulation of typical cellular effector systems. It is thus a fully functional protein, and an intensified cellular activation capacity can be assigned to individuals who carry the 825T allele and who express this protein.

The discovered splice variant Gβ3s-2 can be used to advantage by the corresponding proteins being produced with the objective of developing or testing chemicals which inhibit the protein or prevent its interaction with the G protein alpha or gamma subunits.

Especially in the area of therapy it is a good idea to transfect cells or tissue stably or transiently in the knowledge of the discovered splice variant. Likewise, for therapeutic purposes the Gβ3s-2 splice variant can be expressed in human or animal cells or tissues.

Another use of the nucleic acid sequence of the cDNA shown in Appendix 3 consists in developing gene probes for detection of the nucleic acid sequence.

Furthermore, an antisense construct (oligonucleotide) can be introduced into cells and tissues with the objective of suppressing the synthesis of the Gβ3s-2 splice variant.

Antisense constructs can also be introduced into these cells or tissues with the aid of different vectors (viruses which have been altered by genetic engineering).

What is claimed is:

1. A method for evaluating responsiveness of an individual to treatment with an in vivo pharmaceutical wherein the in vivo pharmaceutical is one which activates G protein heterodimers containing a G protein subunit Gbeta3 or Gbeta3s comprising evaluating the individual for a genetic modification in a gene encoding a Gbeta3 subunit of a protein by detecting the genetic modification in the nucleic acid comprising SEQ ID NO: 2, wherein the genetic modification is a substitution of cytosine by thymidine at position 825 of SEQ ID NO:2, and wherein the thymidine at position 825 of SEQ ID NO: 2 is indicative of the individual having increased activation capacity of G proteins which is indicative of an altered responsiveness of the individual to the treatment with the in vivo pharmaceutical as compared to an individual having a cytosine at position 825 of SEQ ID NO:2.

2. A method for evaluating responsiveness of individual to treatment with in vivo hormones, transmitters, neurotransmitters or pharmaceuticals which activate those G protein heterotrimers which contain the G protein subunits Gbeta3 and Gbeta3s and/or which stimulate the G protein subunit GalphaS comprising evaluating the individual for a genetic modification in a gene encoding a Gbeta3 subunit of a protein, wherein the genetic modification is a substitution of cytosine by thymidine at position 825 of SEQ ID NO:2, wherein the thymidine at position 825 of SEQ ID NO: 2 is indicative of altered responsiveness of the individual to the treatment with the in vivo hormones, transmitters, neurotransmitters or pharmaceuticals which activate those G protein heterotrimers which contain the G protein subunits Gbeta3 and Gbeta3s and/or which stimulate the G protein subunit GalphaS as compared to an individual having a cytosine at position 825 of SEQ ID NO:2.

3. The method of claim 1 or 2, further comprising determining the presence of the Arg16Gly variant and the Gln27Glu variant in the beta2 adrenergic receptor.

4. The method of claim 1, wherein the pharmaceutical is erythropoietin.

5. The method of claim 1, wherein the pharmaceutical is an immunosuppressive and the development of hypertension during said treatment is evaluated.

6. The method of claim 5, wherein the immunosuppressive is cyclosporin.

7. The method of claim 1 or 2, wherein the pharmaceutical is for treatment and prevention of a migraine headache.

8. A method for evaluating responsiveness of an individual to treatment with beta-adrenoceptor blockers comprising evaluating the individual for a genetic modification in a gene encoding a Gbeta3 subunit of a human G protein, wherein the genetic modification is a substitution of cytosine by thymidine at position 825 of SEQ ID NO:2, wherein the presence of thymidine at position 825 of SEQ ID NO: 2 is indicative of the individual having intensified reduction of the cardiac output as a response to treatment with beta-adrenoceptor blockers.

9. A method for evaluating responsiveness of an individual in treatment with a substance having prostoglandin E1 action comprising evaluating the individual for a genetic modification in a gene encoding a Gbeta3subunit of a human G protein, wherein the genetic modification is a substitution of cytosine by thymidine at position 825 of SEQ ID NO:2, wherein the presence of thymidine at position 825 of SEQ ID NO: 2 is indicative of the individual being less responsive to the substance having prostaglandin E1 action.

10. The method of claim 9, wherein the substance is prostaglandin E1.

11. The method of claim 3, wherein the pharmaceutical is for treatment and prevention of a migraine headache.

* * * * *

SEQUENCE LISTING

<160> NUMBER OF SEQ ID NOS: 8

<210> SEQ ID NO 1
<211> LENGTH: 1523
<212> TYPE: DNA
<213> ORGANISM: Homo sapiens

<400> SEQUENCE: 1

```
gggtcgatgg gggagatgga gcaactgcgt caggaagcgg agcagctcaa gaagcagatt      60
gcagatgcca ggaaagcctg tgctgacgtt actctggcag agctggtgtc tggcctagag     120
gtggtgggac gagtccagat gcggacgcgg cggacgttaa ggggacacct ggccaagatt     180
tacgccatgc actgggccac tgattctaag ctgctggtaa gtgcctcgca agatgggaag     240
ctgatcgtgt gggacagcta caccaccaac aaggtgcacg ccatcccact gcgctcctcc     300
tgggtcatga cctgtgccta tgccccatca gggaactttg tggcatgtgg ggggctggac     360
aacatgtgtt ccatctacaa cctcaaatcc cgtgagggca atgtcaaggt cagccgggag     420
ctttctgctc acacaggtta tctctcctgc tgccgcttcc tggatgacaa caatattgtg     480
accagctcgg gggacaccac gtgtgccttg tgggacattg agactgggca gcagaagact     540
gtatttgtgg gacacacggg tgactgcatg agcctggctg tgtctcctga cttcaatctc     600
ttcatttcgg gggcctgtga tgccagtgcc aagctctggg atgtgcgaga ggggacctgc     660
cgtcagactt tcactggcca cgagtcggac atcaacgcca tctgtttctt ccccaatgga     720
gaggccatct gcacgggctc ggatgacgct tcctgccgct tgtttgacct gcgggcagac     780
caggagctga tctgcttctc ccacgagagc atcatctgcg gcatcacgtc cgtggccttc     840
tccctcagtg gccgcctact attcgctggc tacgacgact tcaactgcaa tgtctgggac     900
tccatgaagt ctgagcgtgt gggcatcctc tctggccacg ataacagggt gagctgcctg     960
ggagtcacag ctgacgggat ggctgtggcc acaggttcct gggacagctt cctcaaaatc    1020
tggaactgag gaggctggag aaagggaagt ggaaggcagt gaacacactc agcagccccc    1080
tgcccgaccc catctcattc agtgttctc ttctatattc cgggtgccat tcccactaag     1140
ctttctcctt tgagggcagt ggggagcatg ggactgtgcc tttgggaggc agcatcaggg    1200 acacagggggc aaagaactgc cccatctcct cccatggcct tccctcccca cagtcctcac    1260
agcctctccc ttaatgagca aggacaacct gcccctcccc agcccttgc aggcccagca     1320 gacttgagtc tgaggcccca ggccctagga ttcctccccc agagccacta cctttgtcca    1380 ggcctggtg gtatagggcg tttggccctg tgactatggc tctggcacca ctagggtcct    1440
ggccctcttc ttattcatgc tttctccttt ttctaccttt ttttctctcc taagacacct    1500
gcaataaagt gtagcaccct ggt                                            1523
```

<210> SEQ ID NO 2
<211> LENGTH: 1523
<212> TYPE: DNA

<213> ORGANISM: Homo sapiens

<400> SEQUENCE: 2

| | | | | | |
|---|---|---|---|---|---|
| gggtcgatgg | gggagatgga | gcaactgcgt | caggaagcgg | agcagctcaa | gaagcagatt | 60 |
| gcagatgcca | ggaaagcctg | tgctgacgtt | actctggcag | agctggtgtc | tggcctagag | 120 |
| gtggtgggac | gagtccagat | gcggacgcgg | cggacgttaa | gggacacct | ggccaagatt | 180 |
| tacgccatgc | actgggccac | tgattctaag | ctgctggtaa | gtgcctcgca | agatgggaag | 240 |
| ctgatcgtgt | gggacagcta | caccaccaac | aaggtgcacg | ccatcccact | gcgctcctcc | 300 |
| tgggtcatga | cctgtgccta | tgccccatca | gggaactttg | tggcatgtgg | ggggctggac | 360 |
| aacatgtgtt | ccatctacaa | cctcaaatcc | cgtgagggca | atgtcaaggt | cagccgggag | 420 |
| ctttctgctc | acacaggtta | tctctcctgc | tgccgcttcc | tggatgacaa | caatattgtg | 480 |
| accagctcgg | gggacaccac | gtgtgccttg | tgggacattg | agactgggca | gcagaagact | 540 |
| gtatttgtgg | gacacacggg | tgactgcatg | agcctggctg | tgtctcctga | cttcaatctc | 600 |
| ttcatttcgg | gggcctgtga | tgccagtgcc | aagctctggg | atgtgcgaga | ggggacctgc | 660 |
| cgtcagactt | tcactggcca | cgagtcggac | atcaacgcca | tctgtttctt | ccccaatgga | 720 |
| gaggccatct | gcacgggctc | ggatgacgct | tcctgccgct | tgtttgaccT | gcgggcagac | 780 |
| caggagctga | tctgcttctc | ccacgagagc | atcatctgcg | gcatcacgtc | tgtggccttc | 840 |
| tccctcagtg | gccgcctact | attcgctggc | tacgacgact | tcaactgcaa | tgtctgggac | 900 |
| tccatgaagt | ctgagcgtgt | gggcatcctc | tctggccacg | ataacagggt | gagctgcctg | 960 |
| ggagtcacag | ctgacgggat | ggctgtggcc | acaggttcct | gggacagctt | cctcaaaatc | 1020 |
| tggaactgag | gaggctggag | aaagggaagt | ggaaggcagt | gaacacactc | agcagccccc | 1080 |
| tgcccgaccc | catctcattc | aggtgttctc | ttctatattc | cgggtgccat | tcccactaag | 1140 |
| ctttctcctt | tgagggcagt | ggggagcatg | ggactgtgcc | tttgggaggc | agcatcaggg | 1200 |
| acacagggc | aaagaactgc | cccatctcct | cccatggcct | tccctcccca | cagtcctcac | 1260 |
| agcctctccc | ttaatgagca | aggacaacct | gccccctcccc | agcccttttgc | aggcccagca | 1320 |
| gacttgagtc | tgaggcccca | ggccctagga | ttcctccccc | agagccacta | cctttgtcca | 1380 |
| ggcctgggtg | gtatagggcg | tttggccctg | tgactatggc | tctggcacta | ctagggtcct | 1440 |
| ggccctcttc | ttattcatgc | tttctcctttt | ttctaccttt | ttttctctcc | taagacacct | 1500 |
| gcaataaagt | gtagcaccct | ggt | | | | 1523 |

<210> SEQ ID NO 3
<211> LENGTH: 297
<212> TYPE: PRT
<213> ORGANISM: Homo sapiens

<400> SEQUENCE: 3

Met Gly Glu Met Glu Gln Leu Arg Gln Glu Ala Glu Gln Leu Lys Lys
1               5                   10                  15

Gln Ile Ala Asp Ala Arg Lys Ala Cys Ala Asp Val Thr Leu Ala Glu
            20                  25                  30

Leu Val Ser Gly Leu Glu Val Val Gly Arg Val Gln Met Arg Thr Arg
        35                  40                  45

Arg Thr Leu Arg Gly His Leu Ala Lys Ile Tyr Ala Met His Trp Ala
    50                  55                  60

Thr Asp Ser Lys Leu Leu Val Ser Ala Ser Gln Asp Gly Lys Leu Ile
65                  70                  75                  80

-continued

| | | | | | | | | | | | |
|---|---|---|---|---|---|---|---|---|---|---|---|
|Val|Trp|Asp|Ser|Tyr|Thr|Thr|Asn|Lys|Val|His|Ala Ile Pro Leu Arg|
| | | |85| | | |90| | | |95|

Ser Ser Trp Val Met Thr Cys Ala Tyr Ala Pro Ser Gly Asn Phe Val
            100                 105                 110

Ala Cys Gly Gly Leu Asp Asn Met Cys Ser Ile Tyr Asn Leu Lys Ser
            115                 120                 125

Arg Glu Gly Asn Val Lys Val Ser Arg Glu Leu Ser Ala His Thr Gly
        130                 135                 140

Tyr Leu Ser Cys Cys Arg Phe Leu Asp Asp Asn Asn Ile Val Thr Ser
145                 150                 155                 160

Ser Gly Asp Thr Thr Cys Ala Leu Trp Asp Ile Glu Thr Gly Gln Gln
                165                 170                 175

Lys Thr Val Phe Val Gly His Thr Gly Asp Cys Met Ser Leu Ala Val
            180                 185                 190

Ser Pro Asp Phe Asn Leu Phe Ile Ser Gly Ala Cys Asp Ala Ser Ala
            195                 200                 205

Lys Leu Trp Asp Val Arg Glu Gly Thr Cys Arg Gln Thr Phe Thr Gly
    210                 215                 220

His Glu Ser Asp Ile Asn Ala Ile Cys Phe Phe Ser Leu Ser Gly Arg
225                 230                 235                 240

Leu Leu Phe Ala Gly Tyr Asp Asp Phe Asn Cys Asn Val Trp Asp Ser
                245                 250                 255

Met Lys Ser Glu Arg Val Gly Ile Leu Ser Gly His Asp Asn Arg Val
                260                 265                 270

Ser Cys Leu Gly Val Thr Ala Asp Gly Met Ala Val Ala Thr Gly Ser
        275                 280                 285

Trp Asp Ser Phe Leu Lys Ile Trp Asn
        290                 295

<210> SEQ ID NO 4
<211> LENGTH: 894
<212> TYPE: DNA
<213> ORGANISM: Homo sapiens

<400> SEQUENCE: 4

```
atgggggaga tggagcaact gcgtcaggaa gcggagcagc tcaagaagca gattgcagat      60
gccaggaaag cctgtgctga cgttactctg gcagagctgg tgtctggcct agaggtggtg     120
ggacgagtcc agatgcggac gcggcggacg ttaaggggac acctggccaa gatttacgcc     180
atgcactggg ccactgattc taagctgctg gtaagtgcct cgcaagatgg gaagctgatc     240
gtgtgggaca gctacaccac caacaaggtg cacgccatcc cactgcgctc ctcctgggtc     300
atgacctgtg cctatgcccc atcagggaac tttgtgcat gtggggggct ggacaacatg      360
tgttccatct acaacctcaa atcccgtgag gcaatgtca aggtcagccg ggagctttct      420
gctcacacag ttatctctc ctgctgccgc ttcctggatg acaacaatat tgtgaccagc      480
tcggggaca ccacgtgtgc cttgtgggac attgagactg gcagcagaa gactgtattt       540
gtgggacaca cgggtgactg catgagcctg gctgtgtctc ctgacttcaa tctcttcatt     600
tcggggcct gtgatgccag tgccaagctc tgggatgtgc gagagggac ctgccgtcag       660
actttcactg gccaggagtc ggacatcaac gccatctgtt tcttctccct cagtggccgc     720
ctactattcg ctggctacga cgacttcaac tgcaatgtct gggactccat gaagtctgag     780
cgtgtgggca tcctctctgg ccacgataac agggtgagct gcctgggagt cacagctgac     840
gggatggctg tggccacagg ttcctgggac agcttcctca aaatctggaa ctga           894
```

-continued

```
<210> SEQ ID NO 5
<211> LENGTH: 60
<212> TYPE: DNA
<213> ORGANISM: Homo sapiens

<400> SEQUENCE: 5
ggcctgggtg gtatagggcg tttggccctg tgactatggc tctggcacya ctagggtcct    60

<210> SEQ ID NO 6
<211> LENGTH: 60
<212> TYPE: DNA
<213> ORGANISM: Homo sapiens

<400> SEQUENCE: 6
ttggccctgt gactatggct ctggcacyac tagggtcctg gccctcttct tattcatgct    60

<210> SEQ ID NO 7
<211> LENGTH: 20
<212> TYPE: DNA
<213> ORGANISM: Homo sapiens

<400> SEQUENCE: 7
gccgtcagac tttcactggc                                                20

<210> SEQ ID NO 8
<211> LENGTH: 21
<212> TYPE: DNA
<213> ORGANISM: Homo sapiens

<400> SEQUENCE: 8
tgttcactgc cttccacttc c                                              21
```